United States Patent
Babakhanl et al.

(10) Patent No.: US 12,320,769 B2
(45) Date of Patent: Jun. 3, 2025

(54) SYSTEMS AND METHODS FOR BATTERY-LESS WIRELESSLY POWERED DIELECTRIC SENSORS

(71) Applicant: The Regents of the University of California, Oakland, CA (US)

(72) Inventors: Aydin BabakhanI, Los Angeles, CA (US); Yuxiang Sun, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 654 days.

(21) Appl. No.: 17/287,432

(22) PCT Filed: Nov. 4, 2019

(86) PCT No.: PCT/US2019/059657
§ 371 (c)(1),
(2) Date: Apr. 21, 2021

(87) PCT Pub. No.: WO2020/106440
PCT Pub. Date: May 28, 2020

(65) Prior Publication Data
US 2021/0356417 A1  Nov. 18, 2021

Related U.S. Application Data

(60) Provisional application No. 62/820,770, filed on Mar. 19, 2019, provisional application No. 62/769,166, filed on Nov. 19, 2018.

(51) Int. Cl.
*G01N 27/22* (2006.01)
*A61B 5/00* (2006.01)
(Continued)

(52) U.S. Cl.
CPC ......... *G01N 27/228* (2013.01); *A61B 5/0031* (2013.01); *G01N 27/221* (2013.01);
(Continued)

(58) Field of Classification Search
CPC ........ G01N 27/228; H02J 50/80; H02J 50/20; H02J 50/001; H02J 2310/23; A61B 5/031; A61B 2560/0219
(Continued)

(56) References Cited

U.S. PATENT DOCUMENTS 3,945,387 A   3/1976  Adams
4,220,156 A   9/1980  Morgan et al.
(Continued)

FOREIGN PATENT DOCUMENTS

CN   104767291 A   7/2015
CN   113228464 A   8/2021
(Continued)

OTHER PUBLICATIONS

International Preliminary Report on Patentability dated Sep. 22, 2022 issued in related International Application PCT/US2021/021467, 6 pgs.
(Continued)

*Primary Examiner* — Phallaka Kik
(74) *Attorney, Agent, or Firm* — KPPB LLP

(57) ABSTRACT

Wirelessly powered dielectric sensor in accordance with embodiments of the invention are disclosed. In many embodiments, a wirelessly powered dielectric sensor includes an RF-power receiving antenna that receives electromagnetic power, a power management unit (PMU) including a capacitor to rectify and store the electromagnetic power, and a dielectric constant sensing sensor, where the PMU monitors harvested energy and operates the dielectric sensing sensor; and where the dielectric sensing sensor
(Continued)

senses a dielectric constant of a material that is in close proximity.

20 Claims, 21 Drawing Sheets

(51) Int. Cl.
  *H02J 50/00* (2016.01)
  *H02J 50/20* (2016.01)
  *H02J 50/80* (2016.01)

(52) U.S. Cl.
  CPC ............ *H02J 50/001* (2020.01); *H02J 50/20* (2016.02); *H02J 50/80* (2016.02); *A61B 2560/0219* (2013.01); *H02J 2310/23* (2020.01)

(58) Field of Classification Search
  USPC ........................................................ 320/108
  See application file for complete search history.

(56) References Cited

U.S. PATENT DOCUMENTS

| | | | |
|---|---|---|---|
| 4,301,401 A * | 11/1981 | Roof | G01N 27/221 324/672 |
| 4,388,927 A | 6/1983 | Schober | |
| 4,459,989 A | 7/1984 | Borkan | |
| 4,612,940 A | 9/1986 | Kasevich et al. | |
| 4,719,919 A | 1/1988 | Marchosky et al. | |
| 5,157,340 A * | 10/1992 | Walton | G01N 15/0618 324/641 |
| 5,464,429 A | 11/1995 | Hedberg et al. | |
| 5,497,099 A * | 3/1996 | Walton | F01N 13/0097 324/641 |
| 5,522,865 A | 6/1996 | Schulman et al. | |
| 5,630,426 A | 5/1997 | Eggers et al. | |
| 5,749,909 A | 5/1998 | Schroeppel et al. | |
| 6,402,689 B1 | 6/2002 | Scarantino et al. | |
| 6,423,056 B1 | 7/2002 | Ishikawa et al. | |
| 6,735,472 B2 | 5/2004 | Helland | |
| 6,813,518 B2 | 11/2004 | Kuepper | |
| 6,870,503 B2 | 3/2005 | Mohamadi | |
| 6,882,315 B2 | 4/2005 | Richley et al. | |
| 7,010,340 B2 | 3/2006 | Scarantino et al. | |
| 7,043,301 B1 | 5/2006 | Kroll et al. | |
| 7,132,173 B2 | 11/2006 | Daulton | |
| 7,177,341 B2 | 2/2007 | Mccorkle | |
| 7,180,421 B2 | 2/2007 | Pahlavan et al. | |
| 7,228,228 B2 | 6/2007 | Bartlett et al. | |
| 7,339,883 B2 | 3/2008 | Santhoff et al. | |
| 7,483,735 B2 * | 1/2009 | Liu | G01G 19/50 324/717 |
| 7,610,092 B2 | 10/2009 | Cowan et al. | |
| 7,751,881 B2 | 7/2010 | Cowan et al. | |
| 7,972,117 B1 * | 7/2011 | MacDonald | F04B 49/025 417/40 |
| 8,032,227 B2 | 10/2011 | Parramon et al. | |
| 8,126,418 B2 | 2/2012 | Nowak et al. | |
| 8,188,841 B2 | 5/2012 | Dowla et al. | |
| 8,290,600 B2 | 10/2012 | Hastings et al. | |
| 8,547,248 B2 | 10/2013 | Zdeblick et al. | |
| 8,552,597 B2 | 10/2013 | Song et al. | |
| 8,634,919 B1 | 1/2014 | Hou et al. | |
| 8,644,933 B2 | 2/2014 | Ozawa et al. | |
| 8,670,824 B2 | 3/2014 | Anderson et al. | |
| 8,939,928 B2 | 1/2015 | Savoie et al. | |
| 9,026,212 B2 | 5/2015 | Imran | |
| 9,031,658 B2 | 5/2015 | Chiao et al. | |
| 9,037,223 B2 | 5/2015 | Oral et al. | |
| 9,153,642 B2 | 10/2015 | Li et al. | |
| 9,161,693 B2 | 10/2015 | Rizwan | |
| 9,168,380 B1 | 10/2015 | Greenhut et al. | |
| 9,168,383 B2 | 10/2015 | Jacobson et al. | |
| 9,205,258 B2 | 12/2015 | Simon et al. | |
| 9,270,137 B2 | 2/2016 | Greene | |
| 9,277,874 B2 | 3/2016 | Joshi et al. | |
| 9,421,369 B2 | 8/2016 | Liu et al. | |
| 9,423,438 B2 | 8/2016 | Lin et al. | |
| 9,425,863 B2 * | 8/2016 | Kim | H04B 5/0037 |
| 9,486,621 B2 | 11/2016 | Howard et al. | |
| 9,522,270 B2 | 12/2016 | Perryman et al. | |
| 9,544,068 B2 | 1/2017 | Arbabian et al. | |
| 9,669,223 B2 | 6/2017 | Auricchio et al. | |
| 9,669,230 B2 | 6/2017 | Koop | |
| 9,685,793 B2 | 6/2017 | Zargham et al. | |
| 9,700,712 B2 | 7/2017 | Towe | |
| 9,711,978 B2 | 7/2017 | Manova-elssibony et al. | |
| 9,825,361 B2 * | 11/2017 | Pachler | H01Q 5/357 |
| 9,953,195 B2 | 4/2018 | Turner et al. | |
| 10,014,730 B2 | 7/2018 | Nayak | |
| 10,238,872 B2 | 3/2019 | Pivonka et al. | |
| 10,312,743 B2 | 6/2019 | Ouda et al. | |
| 10,369,369 B2 | 8/2019 | Perryman et al. | |
| 10,493,288 B2 | 12/2019 | Hastings et al. | |
| 10,530,421 B2 | 1/2020 | Muthali et al. | |
| 10,537,403 B2 | 1/2020 | Vora et al. | |
| 10,742,222 B2 | 8/2020 | Emira et al. | |
| 10,742,261 B2 | 8/2020 | Nabki et al. | |
| 10,978,917 B2 | 4/2021 | Freitas et al. | |
| 11,016,051 B1 * | 5/2021 | Sinko | B32B 3/08 |
| 11,048,893 B2 | 6/2021 | Babakhani et al. | |
| 11,050,263 B2 | 6/2021 | Bae et al. | |
| 11,071,857 B2 | 7/2021 | Sun et al. | |
| 11,515,733 B2 | 11/2022 | Babakhani et al. | |
| 11,712,559 B2 | 8/2023 | Sun et al. | |
| 11,911,625 B2 | 2/2024 | Babakhani et al. | |
| 2002/0064245 A1 | 5/2002 | McCorkle | |
| 2002/0103507 A1 | 8/2002 | Helland | |
| 2002/0137991 A1 | 9/2002 | Scarantino et al. | |
| 2003/0032986 A1 | 2/2003 | Kupper | |
| 2004/0054471 A1 | 3/2004 | Bartlett et al. | |
| 2004/0058186 A1 | 3/2004 | Daulton | |
| 2004/0095287 A1 | 5/2004 | Mohamadi | |
| 2004/0108954 A1 | 6/2004 | Richley et al. | |
| 2005/0058121 A1 | 3/2005 | Santhoff et al. | |
| 2005/0256549 A1 | 11/2005 | Holzer | |
| 2006/0136004 A1 | 6/2006 | Cowan et al. | |
| 2007/0118187 A1 | 5/2007 | Denker et al. | |
| 2007/0120677 A1 | 5/2007 | Park et al. | |
| 2007/0211786 A1 | 9/2007 | Shattil | |
| 2007/0225781 A1 | 9/2007 | Saadat et al. | |
| 2007/0293895 A1 | 12/2007 | Cowan et al. | |
| 2008/0021505 A1 | 1/2008 | Hastings et al. | |
| 2008/0039904 A1 | 2/2008 | Beutler et al. | |
| 2008/0252422 A1 | 10/2008 | Dowla et al. | |
| 2008/0262580 A1 | 10/2008 | Gerber et al. | |
| 2008/0300660 A1 | 12/2008 | John | |
| 2008/0306359 A1 | 12/2008 | Zdeblick et al. | |
| 2009/0157141 A1 | 6/2009 | Chiao et al. | |
| 2009/0219139 A1 | 9/2009 | Slesinski | |
| 2009/0292341 A1 | 11/2009 | Parramon et al. | |
| 2010/0076517 A1 | 3/2010 | Imran | |
| 2010/0114243 A1 | 5/2010 | Nowak et al. | |
| 2010/0308974 A1 | 12/2010 | Rowland et al. | |
| 2011/0022025 A1 | 1/2011 | Savoie et al. | |
| 2011/0144851 A1 * | 6/2011 | Gremminger | G01N 33/2888 701/31.4 |
| 2011/0169607 A1 | 7/2011 | Paulson | |
| 2011/0288615 A1 | 11/2011 | Armstrong et al. | |
| 2012/0008714 A1 | 1/2012 | Rizwan | |
| 2012/0071203 A1 * | 3/2012 | Wong | H04M 1/724 455/550.1 |
| 2012/0095531 A1 | 4/2012 | Derbas et al. | |
| 2012/0109236 A1 | 5/2012 | Jacobson et al. | |
| 2012/0161787 A1 * | 6/2012 | Potyrailo | G01N 27/02 29/595 |
| 2012/0166095 A1 * | 6/2012 | Potyrailo | G01N 27/025 977/773 |
| 2012/0183097 A1 * | 7/2012 | Ishizaki | H02J 50/20 307/104 |
| 2012/0197566 A1 * | 8/2012 | Habic | G01N 27/028 702/65 |
| 2012/0239118 A1 | 9/2012 | Ozawa et al. | |

(56) References Cited

U.S. PATENT DOCUMENTS

| | | | |
|---|---|---|---|
| 2012/0256492 A1* | 10/2012 | Song | H02J 50/27 307/64 |
| 2013/0066400 A1 | 3/2013 | Perryman et al. | |
| 2013/0109987 A1 | 5/2013 | Kunis et al. | |
| 2013/0123882 A1 | 5/2013 | Towe | |
| 2013/0197380 A1 | 8/2013 | Oral et al. | |
| 2014/0011286 A1* | 1/2014 | Potyrailo | G01N 33/0031 427/466 |
| 2014/0046389 A1 | 2/2014 | Anderson et al. | |
| 2014/0058239 A1 | 2/2014 | Joshi et al. | |
| 2014/0062666 A1* | 3/2014 | Patterson | G06K 7/10366 340/10.1 |
| 2014/0094674 A1 | 4/2014 | Nurmikko et al. | |
| 2014/0140364 A1* | 5/2014 | Charles | G01K 15/005 374/178 |
| 2014/0198062 A1 | 7/2014 | Kreutzer et al. | |
| 2014/0243848 A1 | 8/2014 | Auricchio et al. | |
| 2014/0252543 A1 | 9/2014 | Li et al. | |
| 2014/0309947 A1* | 10/2014 | Gryska | G01N 33/0047 702/27 |
| 2014/0336474 A1 | 11/2014 | Arbabian et al. | |
| 2014/0375261 A1 | 12/2014 | Manova-Elssibony et al. | |
| 2015/0042358 A1* | 2/2015 | Lin | G01R 27/2623 324/629 |
| 2015/0057557 A1* | 2/2015 | Howie | G16Z 99/00 600/509 |
| 2015/0076920 A1 | 3/2015 | Zargham et al. | |
| 2015/0088115 A1 | 3/2015 | Smith | |
| 2015/0127068 A1 | 5/2015 | Simon et al. | |
| 2015/0130293 A1 | 5/2015 | Hajimiri et al. | |
| 2015/0217123 A1 | 8/2015 | Deterre et al. | |
| 2015/0229139 A1 | 8/2015 | Greene | |
| 2015/0297900 A1 | 10/2015 | Perryman et al. | |
| 2015/0343205 A1 | 12/2015 | Howard, III et al. | |
| 2015/0356332 A1 | 12/2015 | Turner et al. | |
| 2016/0008602 A1 | 1/2016 | Perryman et al. | |
| 2016/0038739 A1 | 2/2016 | Liu et al. | |
| 2016/0048710 A1 | 2/2016 | Nekoogar et al. | |
| 2016/0149441 A1 | 5/2016 | Nayak | |
| 2016/0204765 A1* | 7/2016 | Ferriss | H03J 5/0218 29/600 |
| 2016/0228718 A1 | 8/2016 | Koop | |
| 2016/0267769 A1* | 9/2016 | Rokhsaz | G01N 27/225 |
| 2016/0317060 A1* | 11/2016 | Connor | G16H 20/60 |
| 2016/0338798 A1 | 11/2016 | Vora et al. | |
| 2016/0380754 A1 | 12/2016 | Chen et al. | |
| 2017/0001003 A1 | 1/2017 | Pivonka et al. | |
| 2017/0066334 A1* | 3/2017 | Sindia | B60L 53/12 |
| 2017/0164878 A1* | 6/2017 | Connor | G09B 19/00 |
| 2017/0303505 A1 | 10/2017 | Karsijns et al. | |
| 2018/0069486 A1 | 3/2018 | Ouda et al. | |
| 2018/0071539 A1 | 3/2018 | Hastings et al. | |
| 2018/0123639 A1 | 5/2018 | Muthali et al. | |
| 2018/0140831 A1 | 5/2018 | Feldman et al. | |
| 2018/0143061 A1* | 5/2018 | Strong | G01F 23/284 |
| 2018/0177431 A1 | 6/2018 | Rottenberg | |
| 2018/0235692 A1 | 8/2018 | Efimov et al. | |
| 2018/0256030 A1 | 9/2018 | Lee et al. | |
| 2019/0097323 A1* | 3/2019 | Rokhsaz | H01Q 9/0442 |
| 2019/0097430 A1 | 3/2019 | Bae et al. | |
| 2019/0180065 A1 | 6/2019 | Babakhani et al. | |
| 2019/0224476 A1 | 7/2019 | Sun et al. | |
| 2019/0247050 A1 | 8/2019 | Goldsmith | |
| 2019/0247664 A1 | 8/2019 | Irazoqui et al. | |
| 2019/0262605 A1 | 8/2019 | Babakhani et al. | |
| 2019/0326785 A1 | 10/2019 | Freitas et al. | |
| 2020/0022607 A1 | 1/2020 | Pratt et al. | |
| 2020/0155828 A1 | 5/2020 | Shepard et al. | |
| 2020/0169118 A1* | 5/2020 | Jung | H04B 5/0075 |
| 2020/0195256 A1 | 6/2020 | Emira et al. | |
| 2021/0143678 A1 | 5/2021 | Georgakopoulos | |
| 2021/0339017 A1 | 11/2021 | Sun et al. | |
| 2021/0397257 A1 | 12/2021 | Rogers et al. | |
| 2022/0008736 A1 | 1/2022 | Babakhani et al. | |
| 2022/0158497 A1 | 5/2022 | Babakhani et al. | |
| 2022/0252506 A1 | 8/2022 | Babakhani et al. | |
| 2022/0264196 A1 | 8/2022 | Lyu et al. | |
| 2022/0273944 A1 | 9/2022 | Werneth et al. | |
| 2022/0379124 A1 | 12/2022 | Babakhani et al. | |
| 2023/0081364 A1 | 3/2023 | Babakhani et al. | |
| 2023/0181910 A1 | 6/2023 | Werneth | |
| 2024/0178568 A1* | 5/2024 | Rokhsaz | H01Q 9/0442 |

FOREIGN PATENT DOCUMENTS

| | | | | |
|---|---|---|---|---|
| EP | 3884562 | A1 | 9/2021 | |
| EP | 4032165 | A1 | 7/2022 | |
| EP | 4110165 | A1 | 1/2023 | |
| EP | 4262972 | A1 | 10/2023 | |
| JP | 2002505930 | A | 2/2002 | |
| JP | 2008516741 | A | 5/2008 | |
| JP | 2010527267 | A | 8/2010 | |
| JP | 2022507813 | A | 1/2022 | |
| JP | 2022549118 | A | 11/2022 | |
| JP | 2023515580 | A | 4/2023 | |
| WO | 1996027327 | A1 | 9/1996 | |
| WO | 2000038783 | A1 | 7/2000 | |
| WO | 2007028035 | A2 | 3/2007 | |
| WO | 2007109656 | A2 | 9/2007 | |
| WO | WO-2011030804 | A1 * | 3/2011 | H02J 17/00 |
| WO | 2013058958 | A1 | 4/2013 | |
| WO | 2016199142 | A1 | 12/2016 | |
| WO | 2017059540 | A1 | 4/2017 | |
| WO | 2017066121 | A1 | 4/2017 | |
| WO | 2017070322 | A1 | 4/2017 | |
| WO | 2017205565 | A1 | 11/2017 | |
| WO | 2018039162 | A2 | 3/2018 | |
| WO | 2018053467 | A1 | 3/2018 | |
| WO | 2020106440 | A1 | 5/2020 | |
| WO | 2020106862 | A1 | 5/2020 | |
| WO | 2020125839 | A1 | 6/2020 | |
| WO | 2020106440 | A8 | 7/2020 | |
| WO | 2021005146 | A1 | 1/2021 | |
| WO | 2021007071 | A1 | 1/2021 | |
| WO | 2021007210 | A1 | 1/2021 | |
| WO | 2021046313 | A1 | 3/2021 | |
| WO | 2021055146 | A1 | 3/2021 | |
| WO | 2021174215 | A1 | 9/2021 | |
| WO | 2021183487 | A1 | 9/2021 | |
| WO | 2021247490 | A1 | 12/2021 | |
| WO | 2022133501 | A1 | 6/2022 | |
| WO | 2021174215 | A9 | 9/2022 | |

OTHER PUBLICATIONS

International Preliminary Report on Patentability for International Application PCT/US2021/020343, Report issued Aug. 30, 2022, Mailed on Sep. 9, 2022, 7 Pgs.

International Search Report and Written Opinion for International Application No. PCT/US2022/036926, Search completed Sep. 8, 2022, Mailed Oct. 17, 2022, 07 pgs.

Cogan et al., "Potential-biased, asymmetric waveforms for charge-injection with activated iridium oxide (AIROF) neural stimulation electrodes", IEEE Transactions on Biomedical Engineering, vol. 53, No. 2, Feb. 2006, first published Jan. 23, 2006, pp. 327-332, doi: 10.1109/TBME.2005.862572.

Daubert et al., "2012 EHRA/HRS expert consensus statement on cardiac resynchronization therapy in heart failure: implant and follow-up recommendations and management", Heart Rhythm, vol. 9, No. 9, Sep. 1, 2012, pp. 1524-1576, doi: 10.1016/j.hrthm.2012.07.025.

Li et al., "Parylene-based integrated wireless single-channel neurostimulator", Sensors and Actuators A: Physical, vol. 166, Issue 2, Apr. 2011, pp. 193-200, https://doi.org/10.1016/j.sna.2010.03.003.

Niemann et al., "Longevity of Implantable Pulse Generators in Bilateral Deep Brain Stimulation for Movement Disorders", Neuromodulation, vol. 21, No. 6, Aug. 2018, published online Dec. 19, 2017, pp. 597-603, doi: 10.1111/ner.12743.

(56) References Cited

OTHER PUBLICATIONS

Sun et al., "A two-hop wireless power transfer system with an efficiency-enhanced power receiver for motion-free capsule endoscopy inspection", IEEE Transactions on Biomedical Engineering, vol. 59, No. 11, Nov. 2012, published online Jun. 29, 2012, pp. 3247-3254, doi: 10.1109/TBME.2012.2206809.

Sun et al., "Wirelessly powered implantable pacemaker with on-chip antenna", 2017 IEEE MTT-S International Microwave Symposium (IMS), Jun. 4-9, 2017, pp. 1242-1244, DOI: 10.1109/MWSYM.2017.8058831.

International Preliminary Report on Patentability for International Application PCT/US2019/059657, Report issued May 25, 2021, Mailed on Jun. 3, 2021, 8 Pgs.

International Preliminary Report on Patentability for International Application PCT/US2019/062443, Report issued May 25, 2021, Mailed Jun. 3, 2021, 7 Pgs.

International Preliminary Report on Patentability for International Application PCT/US2020/040283, Report issued Jan. 11, 2022, Mailed on Jan. 20, 2022, 07 Pgs.

International Preliminary Report on Patentability for International Application PCT/US2020/041007, Report issued Jan. 11, 2022, Mailed on Jan. 20, 2022, 06 Pgs.

International Preliminary Report on Patentability for International Application PCT/US2020/048001, Report issued Mar. 15, 2022, Mailed on Mar. 31, 2022, 6 Pgs.

International Search Report and Written Opinion for Application PCT/US2021/35132, completed Aug. 2, 2021, mailed Oct. 4, 2021, 10 pgs.

International Search Report and Written Opinion for International Application No. PCT/US2019/059657, Search completed Dec. 31, 2019, Mailed Jan. 21, 2020, 12 Pgs.

International Search Report and Written Opinion for International Application No. PCT/US2019/062443, Search completed Jan. 15, 2020, Mailed Jan. 29, 2020, 16 Pgs.

International Search Report and Written Opinion for International Application No. PCT/US2020/040283, Search completed Aug. 17, 2020, Mailed Sep. 28, 2020, 17 Pgs.

International Search Report and Written Opinion for International Application No. PCT/US2020/048001, Search completed Oct. 17, 2020, Mailed Nov. 20, 2020, 12 Pgs.

International Search Report and Written Opinion for International Application No. PCT/US2021/020343, Search completed Jun. 2, 2021, Mailed Jun. 22, 2021, 13 Pgs.

International Search Report and Written Opinion for International Application No. PCT/US2021/073036, Search completed Apr. 14, 2022, Mailed May 3, 2022, 18 Pgs.

International Search Report and Written Opinion for International Application PCT/US2017/0047901, filed Aug. 22, 2017, 13 pgs.

International Search Report and Written Opinion for International Application PCT/US2017/052163, filed Sep. 19, 2017, 13 pgs.

International Search Report and Written Opinion for International Application PCT/US2020/049349, mailed Nov. 24, 2020, 7 pgs.

International Search Report and Written Opinion for International Application PCT/US2021/21467, Mailed Jun. 3, 2021, 8 pgs.

International Search Report for International Application No. PCT/US2020/041007, Search completed Aug. 29, 2020, Mailed Oct. 2, 2020, 13 pgs.

Abiri et al., "Inductively powered wireless pacing via a miniature pacemaker and remote stimulation control system", Science Reports, vol. 7, No. 6180, Jul. 21, 2017. pp. 1-10, doi: 10.1038/s41598-017-06493-5.

Agarwal et al., "A 4μW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.

Ahn et al., "Optimal Design of Wireless Power Transmission Links for Millimeter-Sized Biomedical Implants", IEEE Transactions on Biomedical Circuits and Systems, Jan. 20, 2015, vol. 10, Issue 1, pp. 125-137, DOI: 10.1109/TBCAS.2014.2370794.

Arfin et al., "An energy-efficient, adiabatic electrode stimulator with inductive energy recycling and feedback current regulation", IEEE Transactions on Biomedical Circuits and Systems, Feb. 2012, vol. 6, Issue 1, pp. 1-14, first published Oct. 6, 2011, DOI: 10.1109/TBCAS.2011.2166072.

Atzori et al., "The Internet of Things: A survey", Computer Networks, Oct. 2010, vol. 54, Issue 15, pp. 2787-2805, https://doi.org/10.1016/j.comnet.2010.05.010.

Bahrami et al., "Flexible, polarization-diverse UWB antennas for implantable neural recording systems", IEEE Transactions on Biomedical Circuits and Systems, vol. 10, No. 1, Feb. 2016, pp. 38-48.

Balanis, Constantine A., "Antenna Theory: Analysis and Design", John Wiley & Sons, 2016, 1095 pgs., (presented in nine parts).

Bereuter et al., "Hot Topic in Cardiac Devices—Leadless cardiac dual-chamber pacing", Europace Abstracts Supplement, 2018, 1 pg., doi:10.1093/europace/euy015.

Bereuter et al., "Leadless Dual-Chamber Pacing, A Novel Communication Method for Wireless Pacemaker Synchronization", JACC: Basic to Translational Service, Dec. 2018, vol. 3, No. 6, pp. 813-823, https://doi.org/10.1016/j.jacbts.2018.07.009.

Biederman et al., "A Fully-Integrated, Miniaturized (0.125 mm$^2$) 10.5 μW Wireless Neural Sensor", IEEE Journal of Solid-State Circuits, vol. 48, No. 4, Mar. 22, 2013, pp. 960-970, DOI: 10.1109/JSSC.2013.2238994.

Bigio et al., "Microwave absorption spectroscopy of DNA", Biopolymers, Jan. 1993, vol. 33, Issue 1, pp. 147-150, https://doi.org/10.1002/bip.360330114.

Bourdel et al., "A 9-pJ/Pulse 1.42-Vpp OOK CMOS UWB Pulse Generator for the 3.1—10.6-GHz FCC Band", IEEE Transactions on Microwave Theory and Techniques, vol. 58, No. 1, Jan. 2010, pp. 1-9.

Brown et al., "An Ultra-Low-Power 9.8 GHz Crystal-Less UWB Transceiver with Digital Baseband Integrated in 0.18 μm BiCMOS", IEEE International Solid-State Circuits Conference, 2013, pp. 442-443.

Carlson et al., "A 20 mV Input Boost Converter with Efficient Digital Control for Thermoelectric Energy Harvesting", IEEE Journal of Solid-State Circuits, vol. 45, Issue 4, Apr. 2010, pp. 741-750.

Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321.

Chang et al., "27.7 A 30.5mm3 fully packaged implantable device with duplex ultrasonic data and power links achieving 95kb/s with <10-4 BER at 8.5cm depth", IEEE International Solid-State Circuits Conference (ISSCC), Feb. 5-9, 2017, pp. 460-461, DOI: 10.1109/ISSCC.2017.7870460.

Charthad et al., "A mm-sized implantable medical device (IMD) with ultrasonic power transfer and a hybrid bi-directional data link", IEEE Journal of Solid-State Circuits, vol. 50, Issue 8, Aug. 2015, pp. 1741-1753, DOI: 10.1109/JSSC.2015.2427336.

Charthad et al., "A mm-Sized Wireless Implantable Device for Electrical Stimulation of Peripheral Nerves", IEEE Transactions on Biomedical Circuits and Systems, vol. 12, No. 2, Apr. 2018, pp. 257-270, doi: 10.1109/TBCAS.2018.2799623.

Charthad et al., "System-Level Analysis of Far-Field Radio Frequency Power Delivery for mm-Sized Sensor Nodes", IEEE Transactions on Circuits and Systems I: Regular Papers, Feb. 3, 2016, vol. 63, No. 2, pp. 300-311, DOI: 10.1109/TCSI.2015.2512720.

Chen et al., "3D Radar Imaging based on a Synthetic Array of 30GHz Impulse Radiators with On-Chip Antennas in 130nm SiGe BiCMOS", IEEE Transactions on Microwave Theory and Techniques, Nov. 2017, vol. 65, No. 22, pp. 4373-4384.

Chen et al., "Multiple leadless pacemakers implanted in the right ventricle of swine", Europace, 2016, vol. 18, 1748-1752, published online Jan. 31, 2016, doi:10.1093/europace/euv418.

Cheng, "Field and wave electromagnetics", Pearson Education India, 1989, 720 pgs., (presented in three parts).

Chinitz et al., "Accelerometer-based atrioventricular synchronous pacing with a ventricular leadless pacemaker: Results from the Micra atrioventricular feasibility studies", Heart Rhythm, 2018, vol. 15, pp. 1363-1371, https://doi.org/10.1016/j.hrthm.2018.05.004.

(56) References Cited

OTHER PUBLICATIONS

Cogan, "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.

Dagan et al., "A low-power low-cost 24 ghz rfid tag with a c-flash based embedded memory", IEEE Journal of Solid-State Circuits, Sep. 2014, vol. 49, No. 9, pp. 1942-1957, DOI: 10.1109/JSSC.2014.2323352.

Dagdeviren et al., "Conformal piezoelectric energy harvesting and storage from motions of the heart, lung, and diaphragm", PNAS, vol. 111, No. 5, Feb. 4, 2014, published online Jan. 21, 2014, pp. 1927-1932, doi: 10.1073/pnas.1317233111.

De Roover et al., "A fully integrated wireless power supply for pinless active RFID-devices in 130nm CMOS", 2007 IEEE Asian Solid-State Circuits Conference, Nov. 12-14, 2007, pp. 123-126, DOI: 10.1109/ASSCC.2007.4425747.

Deer et al., "The Appropriate Use of Neurostimulation: Avoidance and Treatment of Complications of Neurostimulation Therapies for the Treatment of Chronic Pain", Neuromodulation: Technology at the Neural Interface, Aug. 12, 2014, vol. 17, No. 6, pp. 571-598, DOI: 10.1111/ner.12206.

Derksen et al., "Tissue Discontinuities Affect Conduction Velocity Restitution", Circulation, Aug. 19, 2003, vol. 108, Issue 7, pp. 882-888, https://doi.org/10.1161/01.CIR.0000081766.16185.28.

Dickson, "On-chip high-voltage generation in MNOS integrated circuits using an improved voltage multiplier technique", IEEE Journal of Solid-State Circuits, 1976, vol. 11, No. 3, pp. 374-378, http://dx.doi.org/10.1109/JSSC.1976.1050739.

Dorta-Quinones et al., "A Wireless FSCV Monitoring IC With Analog Background Subtraction and UWB Telemetry", IEEE Transactions on Biomedical Circuits and Systems, vol. 10, No. 2, Apr. 2016, 36 pgs.

Dosdall et al., "Mechanisms of defibrillation", Annual Review of Biomedical Engineering, vol. 12, Aug. 15, 2010, first published as a Review in Advance May 5, 2010, pp. 233-258, https://doi.org/10.1146/annurev-bioeng-070909-105305.

Eldeeb et al., "A 0.4-V Miniature CMOS Current Mode Instrumentation Amplifier", IEEE Transactions on Circuits and Systems—II: Express Briefs, Mar. 2018, Vo. 65, No. 3, pp. 261-265, DOI: 10.1109/TCSII.2017.2685589.

FCC, "First Report and Order 02-48", Federal Communication Commission (FCC), Feb. 2002, 118 pgs., (presented in two parts).

Fenton et al., "Termination of Atrial Fibrillation Using Pulsed Low-Energy Far-Field Stimulation", Circulation, Aug. 11, 2009, vol. 120, Issue 6, pp. 467-476, first published Jul. 27, 2009, https://doi.org/10.1161/CIRCULATIONAHA.108.825091.

Gao et al., "A 71GHZ RF Energy Harvesting Tag with 8% Efficiency for Wireless Temperature Sensors in 65nm CMOS", IEEE Radio Frequency Integrated Circuits Symposium (RFIC), Jun. 2013, pp. 403-406, DOI: 10.1109/RFIC.2013.6569616.

Gilbert, "Impedance matching with lossy components", IEEE Transactions on Circuits and Systems, Feb. 1975, vol. 22, Issue: 2, pp. 96-100, DOI: 10.1109/TCS.1975.1084016.

Grenier et al., "Recent advances in microwave-based dielectric spectroscopy at the cellular level for cancer investigations", IEEE Transactions on Microwave Theory and Techniques, Apr. 11, 2013, vol. 61, No. 5, pp. 2023-2030, doi:ff10.1109/TMTT.2013.2255885.

Guler et al., "Power Management in Wireless Power-Sipping Devices: A Survey", IEEE Circuits and Systems Magazine, Nov. 20, 2017, pp. 64-82, DOI: 10.1109/MCAS .2017.2757090.

Gunturi et al., "A 250-Mb/s Data Rate IR-UWB Transmitter Using Current- Reused Technique", IEEE Transactions on Microwave Theory and Techniques, vol. 65, No. 11, Nov. 2017, pp. 4255-4265, DOI:10.1109/TMTT.2017.2695189.

Hannan et al., "Energy harvesting for the implantable biomedical devices: issues and challenges", BioMedical Engineering OnLine, 2014, vol. 13, No. 79, 23 pgs., https://doi.org/10.1186/1475-925X-13-79.

Hehn et al., "A Fully Autonomous Integrated Interface Circuit for Piezoelectric Harvesters", IEEE Journal of Solid-State Circuits, Sep. 2012, vol. 47, Issue 9, pp. 2185-2198, DOI: 10.1109/JSSC.2012.2200530.

Higgins et al., "Advances in Pacing Therapy: Examining the Potential Impact of Leadless Pacing Therapy", Journal of Innovations in Cardiac Rhythm Management, Nov. 2014, vol. 5, pp. 1825-1833, DOI: 10.19102/icrm.2014.051106.

Ho et al., "Wireless power transfer to deep-tissue microimplants", PNAS, vol. 111, No. 22, Jun. 3, 2014, first published May 19, 2014, pp. 7974-7979, https://doi.org/10.1073/pnas.1403002111.

Huang et al., "A simple subthreshold cmos voltage reference circuit with channel-length modulation compensation", IEEE Transactions on Circuits and Systems—II: Express Briefs, Sep. 2006, vol. 53, No. 9, pp. 882-885, DOI: 10.1109/TCSII.2006.881813.

Huang et al., "Materials and designs for wireless epidermal sensors of hydration and strain", Advanced Functional Materials, Jul. 2, 2014, vol. 24, Issue 25, pp. 3846-3854, first published Mar. 2, 2014, doi: 10.1002/adfm.201303886.

Huang et al., "Neurostimulation Strategy for Stress Urinary Incontinence", IEEE Transactions on Neural Systems and Rehabilitation Engineering, Jul. 2017, vol. 25, No. 7, pp. 1068-1078, first published Mar. 7, 2017, doi: 10.1109/TNSRE.2017.2679077.

Jawad et al., "Opportunities and Challenges for Near-Field Wireless Power Transfer: A Review", Energies, vol. 10, No. 1022, Jul. 18, 2017, 28 pgs., doi:10.3390/en10071022.

Jeon et al., "A 143nW Glucose-Monitoring Smart Contact Lens IC with a Dual-Mode Transmitter for Wireless-Powered Backscattering and RF-Radiated Transmission Using a Single Loop Antenna", Symposium on VLSI Circuits, Jun. 9-14, 2019, pp. C294-C295, DOI: 10.23919/VLSIC.2019.8777984.

Jia et al., "A mm-sized free-floating wirelessly powered implantable optical stimulating system-on-a-chip", 2018 IEEE International Solid—State Circuits Conference—(ISSCC), Feb. 11-15, 2018, San Francisco, CA, pp. 468-470, DOI: 10.1109/ISSCC.2018.8310387.

Jiang et al., "A Sub-1 µW Multiparameter Injectable BioMote for Continuous Alcohol Monitoring", IEEE Custom Integrated Circuits Conference (CICC), 2018, pp. 1-4.

Johnson et al., "StimDust: A 6.5 mm3, wireless ultrasonic peripheral nerve stimulator with 82% peak chip efficiency", UC Berkeley, Retrieved from https://escholarship.org/uc/item/8px811qc, published May 5, 2019, 5 pgs., http://dx.doi.org/10.1109/CICC.2018.8357047.

Kang et al., "A 1.7x4.1x2 mm3 Fully Integrated pH Sensor for Implantable Applications Using Differential Sensing and Drift-Compensation", 2019 Symposium on VLSI Circuits Digest of Technical Papers, C25-1, pp. C310-C311.

Kang et al., "Design and Optimization of Area-Constrained Wirelessly Powered CMOS UWB SoC for localization applications", IEEE Transactions on Microwave Theory and Techniques, Apr. 2016, vol. 64, No. 4, pp. 1042-1054, DOI: 10.1109/TMTT.2016.2536663.

Karthaus et al., "Fully Integrated Passive UHF RFID Transponder IC with 16.7-µW Minimum RF Input Power", IEEE Journal of Solid State Circuits, Oct. 2003, vol. 38, No. 10, pp. 1602-1608, DOI: 10.1109/JSSC.2003.817249.

Kelly et al., "A power-efficient neural tissue stimulator with energy recovery", IEEE Transactions on Biomedical Circuits and Systems, Feb. 2011, vol. 5, Issue 1, pp. 20-29, first published Jan. 24, 2011, DOI: 10.1109/TBCAS.2010.2076384.

Kennedy et al., "High intensity focused ultrasound: surgery of the future?", British Journal of Radiology, Sep. 2003, vol. 76, No. 909, pp. 590-599, doi: 10.1259/bjr/17150274.

Razavi, Behzad, "Rf Microelectronics", New Jersey: Prentice Hall, 1998, vol. 1, 98 pgs., Chapter 8: pp. 497-594.

Rodriguez et al, "Long-term results of electrical stimulation of the lower esophageal sphincter for the treatment of gastroesophageal reflux disease", Endoscopy, Aug. 2013, vol. 45, No. 8, pp. 595-604, DOI: 10.1055/s-0033-1344213.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554, DOI:10.1109/TIE.2010.2046002.

(56) References Cited

OTHER PUBLICATIONS

Sankaragomathi et al., "A 27w subcutaneous wireless biosensing platform with optical power and data transfer", Proceedings of the IEEE 2014 Custom Integrated Circuits Conference, Sep. 15, 2014, pp. 1-4.
Sayenko et al., "Spinal segment-specific transcutaneous stimulation differentially shapes activation pattern among motor pools in humans", Journal of Applied Physiology, 2015, vol. 118, pp. 1364-1374, first published Mar. 26, 2015; doi:10.1152/japplphysiol.01128.2014.
Shi et al., "A 10 mm3 Inductive Coupling Radio for Syringe-Implantable Smart Sensor Nodes", IEEE Journal of Solid-State Circuits, Nov. 2016, vol. 51, No. 11, pp. 2570-2583, DOI: 10.1109/JSSC.2016.2606162.
Shi et al., "A 10mm3 syringe-implantable near-field radio system on glass substrate", IEEE Int. Solid-State Circuits Conf. (ISSCC) Dig. Tech. Papers, pp. 448-449, Feb. 2016.
Silvetti et al., "Cardiac pacing in paediatric patients with congenital heart defects: transvenous or epicardial?", Europace, vol. 15, No. 9, Sep. 2013, published online Feb. 24, 2013, pp. 1280-1286, doi: 10.1093/europace/eut029.
Soontornpipit, "Design of an Implantable Antenna Feasibility Study for Continuous Glucose Monitoring", ECTI Transactions on Electrical Engineering, Electronics, and Communications, Feb. 2014, vol. 12, No. 1, pp. 44-52.
Stoopman et al., "Co-Design of a CMOS Rectifier and Small Loop Antenna for Highly Sensitive RF Energy Harvesters", IEEE Journal of Solid-State Circuits, Mar. 2014, vol. 49, Issue 3, pp. 622-634, DOI: 10.1109/JSSC.2014.2302793.
Sun et al., "A wirelessly powered injection-locked oscillator with on-chip antennas in 180nm SOI CMOS", 2016 IEEE MTT-S International Microwave Symposium (IMS), Aug. 11, 2016, pp. 1-3 [online], [retrieved on Aug. 14, 2020]. Retrieved from the Internet <URL: https://ieeexplore.ieee.org/abstract/document/7540249>, entire document.
Sun et al., "A Wirelessly Powered Injection-Locked Oscillator With On-Chip Antennas in 180-nm SOI CMOS for Spectroscopy Application", IEEE Sensors Letters, vol. 3, No. 7, Jul. 3, 2019, pp. 1-4 [online], [retrieved on Aug. 14, 2020]. Retrieved from the Internet <URL: https://ieeexplore.ieee.org/abstract/document/8754750>.
Tabesh et al., "A Power-Harvesting Pad-Less Millimeter-Sized Radio", IEEE Journal of Solid-State Circuits, Apr. 2015, vol. 50, Issue 4, pp. 962-977, DOI: 10.1109/JSSC.2014.2384034.
Teh et al., "Design and analysis of UHF micropower CMOS DTMOST rectifiers", IEEE Transactions on Circuits and Systems—II: Express Briefs, Feb. 2009, vol. 56, No. 2, pp. 122-126, doi: 10.1109/TCSII.2008.2010190.
Theilmann et al., "A µW Complementary Bridge Rectifier With Near Zero Turn-on Voltage in SOS CMOS for Wireless Power Supplies", IEEE Transactions on Circuits and Systems I: Regular Papers, 2012, vol. 59, No. 9, pp. 2111-2124, DOI: 10.1109/TCSI.2012.2185293.
Tjong et al., "Permanent Leadless Cardiac Pacemaker Therapy A Comprehensive Review", Circulation, Apr. 11, 2017, vol. 135, pp. 1458-1470, DOI: 10.1161/CIRCULATIONAHA.116.025037.
Tolosa et al., "Electrochemically deposited iridium oxide reference electrode integrated with an electroenzymatic glutamate sensor on a multi-electrode array microprobe", Biosensors and Bioelectronics, 2013, vol. 42, pp. available online Nov. 6, 2012, pp. 256-260, http://dx.doi.org/10.1016/jbios.2012.10.061.
Van Dongen et al., "Does a coupling capacitor enhance the charge balance during neural stimulation? An empirical study", Medical & Biological Engineering and Computing, 2016, vol. 54, pp. 93-101, published online May 29, 2015, DOI 10.1007/s11517-015-1312-9.
Van Rees et al., "Implantation-related complications of implantable cardioverter-defibrillators and cardiac resynchronization therapy devices: a systematic review of randomized clinical trials", Journal of the American College of Cardiology, Aug. 30, 2011, vol. 58, Issue 10, pp. 995-1000, https://doi.org/10.1016/j.jacc.2011.06.007.
Wan et al., "Analysis and design of a thermoelectric energy harvesting system with reconfigurable array of thermoelectric generators for IoT applications", IEEE Transactions on Circuits and Systems I: Regular Papers, Sep. 2017, vol. 64, No. 9, pp. 2346-2358, DOI: 10.1109/TCSI.2017.2708763.
Weber et al., "A Miniaturized Single-Transducer Implantable Pressure Sensor With Time-Multiplexed Ultrasonic Data and Power Links", IEEE Journal of Solid-State Circuits, Apr. 2018, vol. 53, No. 4, pp. 1089-1101, DOI: 10.1109/JSSC.2017.2782086.
Weber et al., "Functional electrical stimulation using microstimulators to correct foot drop: a case study1", Canadian Journal of Physiology and Pharmacology, 2004, vol. 82, No. 8-9, first published Oct. 19, 2004, pp. 784-792, doi: 10.1139/Y04-078.
Xie et al., "Wireless power transfer and applications to sensor networks", IEEE Wireless Communications, Aug. 2013, vol. 20, Issue 4, pp. 140-145, DOI: 10.1109/MWC.2013.6590061.
Xu et al., "A fully implantable stimulator with wireless power and data transmission for experimental investigation of epidural spinal cord stimulation", IEEE Transactions on Neural Systems and Rehabilitation Engineering, 2015, vol. 23, No. 4, pp. 683-692, DOI: 10.1109/TNSRE.2015.2396574.
Yadav et al., "Low Voltage Low Power Sub-threshold Operational Amplifier in 180nm CMOS", 2017 IEEE Third International Conference on Sensing signal Processing and Security (ICSSS), 2017, 4 pgs.
Yi et al., "Analysis and design strategy of UHF micro-power CMOS rectifiers for micro-sensor and RFID applications", IEEE Transactions on Circuits and Systems I: Regular Papers, Jan. 15, 2007, vol. 54, Issue 1, pp. 153-166, DOI: 10.1109/TCSI.2006.887974.
Yu et al., "Cardiac resynchronization therapy: state of the art 2013", European Heart Journal, vol. 34, Issue 19, May 14, 2013, online published Jan. 25, 2013, pp. 1396-1403, https://doi.org/10.1093/eurheartj/ehs454.
Yvanoff et al., "A Feasibility Study of Tissue Characterization Using Implanted LC Sensors", IEEE Transactions on Antennas and Propagation, Apr. 2009, vol. 57, Issue 4, pp. 885-893, DOI: 10.1109/TAP.2009.2016073.
Zargham et al., "Fully Integrated On-Chip Coil in 0.13 µm CMOS for Wireless Power Transfer Through Biological Media", IEEE Transactions on Biomedical Circuits and Systems, Apr. 2015, vol. 9, Issue 2, pp. 259-271, DOI: 10.1109/TBCAS.2014.2328318.
Zhang et al., "A 23 µA RF-powered transmitter for biomedical applications", 2011 IEEE Radio Frequency Integrated Circuits Symposium, 4 pgs., DOI: 10.1109/RFIC.2011.5940711.
Zhang et al., "A Miniature Mode Reconfigurable Inductorless IR-UWB Transmitter—Receiver for Wireless Short-Range Communication and Vital-Sign Sensing", IEEE Journal of Emerging and Selected Topics in Circuits and Systems, vol. 8, No. 2, Jun. 2018, pp. 294-305.
Kim et al., "A 144-MHz Fully Integrated Resonant Regulating Rectifier With Hybrid Pulse Modulation for mm-Sized Implants", IEEE Journal of Solid-State Circuits, Nov. 2017, vol. 52, Issue 11, pp. 3043-3055, DOI: 10.1109/JSSC.2017.2734901.
Kim et al., "Design of miniaturized wireless power receivers for mm-sized implants", 2017 IEEE Custom Integrated Circuits Conference (CICC), Apr. 30-May 30, 2017, 8 pgs., DOI: 10.1109/CICC.2017.7993703.
Kim et al., "Wireless power transfer to a cardiac implant", Applied Physics Letters, vol. 101, 2012, pp. 073701-1-073701-4; doi: 10.1063/1.4745600.
Kocer et al., "A new transponder architecture with on-chip ADC for long- range telemetry applications", IEEE Journal of Solid-State Circuits, vol. 41, No. 5, Apr. 24, 2006, pp. 1142-1148 [online], [retrieved on Aug. 14, 2020]. Retrieved from the Internet <URL: https://www.mpflynngroup.com/uploads/7/3/4/9/73490609/01624404.pdf>,, entire document, especially: fig. 1, p. 1, col. 2, para 3; p. 2, col. 2, para 2.
Kotani et al., "High-Efficiency Differential-Drive CMOS Rectifier for UHF RFIDs", IEEE Journal of Solid-State Circuits, Nov. 2009, vol. 44, Issue 11, pp. 3011-3018, DOI: 10.1109/JSSC.2009.2028955.
Kulkarni et al., "A 750 Mb/s, 12 pJ/b, 6-to-10 GHz CMOS IR-UWB Transmitter with Embedded On-Chip Antenna", IEEE Journal of Solid-State Circuits, vol. 44, No. 2, Feb. 2009, pp. 394-403, DOI: 10.1109/JSSC.2008.2011034.

(56) References Cited

OTHER PUBLICATIONS

Kuo et al., "Near-field power transfer and backscattering communication to miniature RFID tag in 65 nm CMOS technology", 2016 IEEE MTT-S International Microwave Symposium (IMS), May 22-27, 2016, 4 pgs., DOI: 10.1109/MWSYM.2016.7540221.

Kurs et al., "Wireless Power Transfer via Strongly Coupled Magnetic Resonances", Science, vol. 317, No. 5834, Jul. 6, 2007, published online Jun. 7, 2007, pp. 83-86, DOI: 10.1126/science.1143254.

Le et al., "Efficient Far-Field Radio Frequency Energy Harvesting for Passively Powered Sensor Networks", IEEE Journal of Solid-State Circuits, May 2008, vol. 43, No. 5, pp. 1287-1302, DOI: 10.1109/JSSC.2008.920318.

Lepock, "Cellular effects of hyperthermia: relevance to the minimum dose for thermal damage", International Journal of Hyperthermia, vol. 19, No. 3, May-Jun. 2003, pp. 252-266, DOI: 10.1080/0265673031000065042.

Li et al., "A 13.56 MHz Wireless Power Transfer System with Reconfigurable Resonant Regulating Rectifier and Wireless Power Control for Implantable Medical Devices", IEEE Journal of Solid-State Circuits, vol. 50, No. 4, Apr. 1, 2015, pp. 978-989.

Liu et al., "A 650-pJ/bit MedRadio transmitter with an FIR-embedded phase modulator for medical micro-power networks (MMNs)", IEEE Transactions on Circuits and Systems I: Regular Papers, 2013, vol. 60, No. 12, pp. 3279-3288, DOI: 10.1109/TCSI.2013.2265970.

Lo et al., "A fully integrated wireless SoC for motor function recovery after spinal cord injury", IEEE Transactions on Biomedical Circuits and Systems, Jun. 2017, vol. 11, Issue 3, pp. 497-509, first published May 23, 2017, DOI: 10.1109/TBCAS.2017.2679441.

Lo et al., "Bio-Impedance Characterization Technique with Implantable Neural Stimulator Using Biphasic Current Stimulus", Conference Proceedings of the IEEE Engineering in Medicine and Biology Society, 2014, pp. 474-477, doi: 10.1109/EMBC.2014.6943631.

Lonappan et al., "Nondestructive Measurement of Human Blood at Microwave Frequencies", Journal of Electromagnetic Waves and Applications, 2007, vol. 21, Issue 8, pp. 1131-1139, DOI: 10.1163/156939307781749740.

Lopez-Lapena et al., "A closed-loop maximum power point tracker for subwatt photovoltaic panels", IEEE Transactions on Industrial Electronics, Mar. 2012, vol. 59, No. 3, pp. 1588-1596, DOI: 10.1109/TIE.2011.2161254.

Lu et al., "Flexible Neural Electrode Array Based-on Porous Graphene for Cortical Microstimulation and Sensing", Scientific Reports, Sep. 19, 2016, vol. 6, No. 33526, 9 pgs., DOI: 10.1038/srep33526.

Lu et al., "Ultra-flexible Piezoelectric Devices Integrated with Heart to Harvest the Biomechanical Energy", Scientific Reports, Nov. 5, 2015, 9 pgs. https://doi.org/10.1038/srep16065.

Lyu et al., "A 430-Mhz Wirelessly Powered Implantable Pulse Generator With Intensity/Rate Control and Sub-1 µA Quiescent Current Consumption", IEEE Transactions on Biomedical Circuits and Systems, vol. 13, No. 1, Feb. 2019, pp. 180-190, DOI: 10.1109/TBCAS.2018.2879357.

Lyu et al., "A 915-MHz Far-Field Energy Harvester with -22-dBm Sensitivity and 3-V Output Voltage Based on Antenna-and-Rectified Codesign", IEEE Microwave and Wireless Components Letters, Aug. 2019, vol. 29, No. 8, pp. 557-559, DOI: 10.1109/LMWC.2019.2923685.

Lyu et al., "A Multi-site Heart Pacing Study Using Wirelessly Powered Leadless Pacemakers", IEEE Xplore, Year: 2018, Date: Oct. 29, 2018 (retrieved on Jan. 15, 2020), 6 pgs.

Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, DOI: 10.1109/TBCAS.2018.2852680.

Lyu et al., "Synchronized Biventricular Heart Pacing in a Closed-chest Porcine Model based on Wirelessly Powered Leadless Pacemakers", Scientific Reports, 10, Article No. 2067, 2020, 13 pgs.

Lyu et al., "Towards the Implementation of a Wirelessly Powered Dielectric Sensor with Digitized Output for Implantable Applications", IEEE Sensors Letters, Mar. 2019, vol. 3, No. 3, pp. 1-4, first published Jan. 30, 2019.

Mandal et al., "Low-power CMOS rectifier design for RFID applications", IEEE Transactions on Circuits and Systems I: Regular Papers, Jul. 2007, vol. 54, No. 6, pp. 1177-1188, DOI:10.1109/TCSI.2007.895229.

Meyer et al., "First in a series on the leadless pacing: Percutaneous implantable transcatheter pacemaker—background, technical aspects, and possible pitfalls", d-Journal of Cardiology Practice, Aug. 23, 2016, vol. 14, No. 20, 18 pgs.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015.2466592.

Mirzavand et al., "High-Resolution Dielectric Sensor Based on Injection-Locked Oscillators", IEEE Sensors Journal, Jan. 1, 2018, vol. 18, Issue 1, pp. 141-148, published online published Nov. 13, 2017, DOI: 10.1109/JSEN.2017.2772923.

Montgomery et al., "Wirelessly powered, fully internal optogenetics for brain, spinal and peripheral circuits in mice", Nature Methods, 2015, vol. 12, No. 10, pp. 969-974, published online Aug. 17, 2015, DOI: 1031038/NMETH.3536.

Pandey et al., "A Sub-100 µW MICS/ISM Band Transmitter Based on Injection-Locking and Frequency Multiplication", IEEE Journal of Solid-State Circuits, May 2011, vol. 46, Issue 5, pp. 1049-1058, first published Apr. 5, 2011, DOI: 10.1109/JSSC.2011.2118030.

Papotto et al., "A 90nm CMOS 5mb/s crystal-less rf transceiver for rf-powered wsn nodes", 2012 IEEE International Solid-State Circuits Conference, Feb. 19-23, 2012, pp. 451-453, DOI: 10.1109/ISSCC.2012.6177087.

Paul, "Inductance: loop and partial", John Wiley & Sons, 2011, 395 pgs., (presented in two parts).

Pellerano et al., "A mm-Wave Power-Harvesting RFID Tag in 90 nm CMOS", IEEE Journal of Solid-State Circuits, Aug. 2010, vol. 45, Issue 8, pp. 1627-1637, DOI: 10.1109/JSSC.2010.2049916.

Pozar, David M., "Microwave Engineering", John Wiley & Sons, Inc., Third Edition, 2005, 105 pgs., Chapter 13: p. 604, Chapter 14: p. 658.

Radiom et al., "Far-Field On-Chip Antennas Monolithically Integrated in a Wireless-Powered 5.8-GHz Downlink/UWB Uplink RFID Tag in 0.18-µm Standard CMOS", IEEE Journal of Solid-State Circuits, Sep. 2010, vol. 45, Issue 9, pp. 1746-1758, DOI: 10.1109/JSSC.2010.2055630.

Rahmani et al., "A 1.6mm3 Wirelessly Powered Reconfigurable FDD Radio with On-Chip Antennas Achieving 4.7 pJ/b TX and 1 pJ/b RX Energy Efficiencies for Medical Implants", Conference: 2020 IEEE Custom Integrated Circuits Conference (CICC), Apr. 2020, 4 pgs., DOI:10.1109/CICC48029.2020.9075935.

Rahmani et al., "A Dual-Mode RF Power Harvesting System With an On-Chip Coil in 180-nm SOI CMOS for Millimeter-Sized Biomedical Implants", IEEE Transactions on Microwave Theory and Techniques, Oct. 2018, vol. 67, No. 1, pp. 414-428, DOI:10.1109/TMTT.2018.2876239.

Rahmani et al., "A Wireless Power Receiver with an On-chip Antenna for Millimeter-size Biomedical Implants in 180 nm SOI CMOS", in 2017 IEEE MTT-S International Microwave symposium (IMS), Jun. 2017, pp. 300-303.

Rahmat-Samii et al., "Implanted antennas in medical wireless communications", Synthesis Lectures on Antennas, 2005, 1.1 pp. 1-82.

Rajavi et al., "An RF-powered FDD radio for neural microimplants", IEEE Journal of Solid-State Circuits, May 2017, vol. 52, Issue: 5, pp. 1221-1229, DOI: 10.1109/JSSC.2016.2645601.

Ramrakhyani et al., "Design and Optimization of Resonance-Based Efficient Wireless Power Delivery Systems for Biomedical Implants", IEEE Transactions on Biomedical Circuits and Systems, vol. 5, No. 1, Feb. 2011, pp. 48-63.

Randles, "Kinetics of rapid electrode reactions", Discussions of the Faraday Society, 1947, vol. 1, pp. 11-19.

(56) References Cited

OTHER PUBLICATIONS

Rategh et al., "Superharmonic Injection-Locked Frequency Dividers", IEEE Journal of Solid-State Circuits, Jun. 1999, vol. 34, No. 6, pp. 813-821.
Razavi, "Design of analog CMOS Integrated Circuits", McGraw-Hill Series in Electrical and Computer Engineering, 2001, 706 pgs., (presented in eight parts).
Extended European Search Report for European Application No. 21908064.5, Search completed Nov. 29, 2024, Mailed Dec. 9, 2024, 13 Pgs.
Ahmadi et al., "A Class-E Power Amplifier With Wideband FSK Modulation for Inductive Power and Data Transmission to Medical Implants", Ieee Sensors Journal, Ieee, USA, Sep. 1, 2018, vol. 18, No. 17, pp. 7242-7252, XP011688526, ISSN: 1530-437X, DOI: 0.1109/JSEN.2018.2851605.
Ghovanloo et al., "A Wireless Implantable Multichannel Microstimulating System-on-a-Chip With Modular Architecture", IEEE Transactions on Neural Systems and Rehabilitation Engineering IEEE, USA, Sep. 1, 2007, vol. 15, No. 3, pp. 449-457, XP011348056, ISSN: 1534-4320, DOI: 10.1109/TNSRE.2007.903970.
Kim et al., "Integrated Wireless Neural Interface Based on the Utah Electrode Array", Biomedical Microdevices, Kluwer Academic Publishers, BO, Dec. 10, 2008, vol. 11, No. 2, pp. 453-466, XP019670986, ISSN: 1572-8781.
Muller et al., "A Minimally Invasive 64-Channel Wireless uECoG Implant", IEEE Journal of Solid-State Circuits, Jan. 1, 2015, vol. 50, No. 1, pp. 344-359, XP011568753, ISSN: 0018-9200, DOI: 10.1109/JSSC.2014.2364824.
Piedade et al., "Visual Neuroprosthesis: a Non Invasive System for Stimulating the Cortex", IEEE transactions on Circuits and Systems Part I: Regular Papers, Dec. 1, 2005, pp. 2648-2662, XP055886580, ISSN: 1057-7122, DOI: 10.1109/TCSI.2005.857923.
Song et al., "A Brain Implantable Microsystem with Hybrid RF/IR Telemetry for Advanced Neuroengineering Applications", 2009 Annual International Conference of the Ieee Engineering in Medicine and Biology Society, Aug. 1, 2007, pp. 445-448, XP055135982, ISSN: 1557-170X, DOI: 10.1109/IEMBS.2007.4352319.
Sutardja et al., "Isolator-Less Near-Field RFID Reader for Sub-Cranial Powering/Data Link of Millimeter-Sized Implants", Ieee Journal of Solid-State Circuits, Ieee, USA, Jul. 1, 2018, vol. 53, No. 7, pp. 2032-2042, XP011685915, ISSN: 0018-9200, DOI: 10.1109/JSSC.2018.2822673.
Wong et al., "Cmos Stimulating Chips Capable of Wirelessly Driving 473 Electrodes for a Cortical Vision Prosthesis", Journal of Neural Engineering, Institute of Physics Publishing, Bristol, GB, Feb. 19, 2019, vol. 16, No. 2, p. 26025, XP020339940, ISSN: 1741-2552, DOI: 10.1088/1741-2552/AB021B.
Yang et al., "Challenges in Scaling Down of Free-Floating Implantable Neural Interfaces to Millimeter Scale", Ieee Access, Ieee, USA, Jul. 6, 2020, vol. 8, pp. 133295-133320, XP011801127, DOI: 10.1109/ACCESS.2020.3007517.
Extended European Search Report for European Application No. 21759630.3, Search completed Apr. 2, 2024, Mailed Apr. 12, 2024, 8 Pgs.
Akin et al., "A Telemetrically Powered and Controlled Implantable Neural Recording System with CMOS Interface Circuitry", Proceedings of the Mediterranean Electrotechnical Conference. Antalya, Turkey, New York, IEEE, US, vol. 2, No. ISBN: 978-0-7803-1772-6, Apr. 12, 1994, pp. 545-548, XP000506184.
Extended European Search Report dated Jul. 19, 2022, issued in related European Application No. 19887763.1, 7 pgs.
Extended European Search Report for European Application No. 20860681.4, Search completed Jul. 26, 2023, Mailed Aug. 2, 2023, 7 pgs.
Extended European Search Report for European Application No. 20866392.2, Search completed Aug. 31, 2023, Mailed Sep. 11, 2023, 5 pgs.
International Preliminary Report on Patentability for International Application PCT/US2021/073036, Report issued Jun. 13, 2023, Mailed on Jun. 29, 2023, 10 pgs.

Andersen et al., "A 118-mw pulse-based radar soc in 55-nm cmos for non-contact human vital signs detection", IEEE Journal of Solid-State Circuits, vol. 52, No. 12, 2017, pp. 3421-3433.
Bahrami et al., "System Level Design of a Full-Duplex Wireless Transceiver for Brain-Machine Interfaces", IEEE Transactions on Microwave Theory and Techniques, vol. 64, No. 10, Oct. 2016, 10 pgs.
Besnoff et al., "Battery-free multichannel digital ECG biotelemetry using UHF RFID techniques", 2013 IEEE International Conference on RFID, 2013, pp. 16-22.
Bourdel et al., "A 9-pJ/pulse 1.42-Vpp OOK CMOS UWB pulse generator for the 3.1-10.6-GHz FCC band", IEEE Transactions on Microwave Theory and Techniques, vol. 58, No. 1, 2009, pp. 65-73.
Chae et al., "A 128- channel 6 mW wireless neural recording IC with spike feature extraction and UWB transmitter", IEEE Transactions on Neural Systems and Rehabilitation Engineering, vol. 17, No. 4, 2009, pp. 312-321.
Choi et al., "A Wirelessly Powered Microspectrometer for Neural Probe-Pin Device.", Micro+Nano Materials, Devices, and Systems, 2015, vol. 9668. SPIE, 8 pgs.
Cruz et al., "Hybrid UHF/UWB antenna for passive indoor identification and localization systems", IEEE Transactions on Antennas and Propagation, vol. 61, No. 1, 2013, pp. 354-361.
Hagen et al., "Multimodal Modeling of Neural Network Activity: Computing LFP, ECoG, EEG, and MEG Signals With LFPy 2.0", Frontiers in Neuroinformatics, vol. 12, No. 92, 2018, 59 pgs.
Harrison, Reid, "The Design of Integrated Circuits to Observe Brain Activity", Proceedings of the IEEE, vol. 96, No. 7, Jul. 2008, pp. 1203-1216.
Huang et al., "A 1-μW 10-bit 200-kS/s SAR ADC With a Bypass Window for Biomedical Applications", IEEE Journal of Solid-State Circuits, vol. 47, No. 11, Nov. 2012, pp. 2783-2795.
Koski et al., "Fundamental Characteristics of Electro-Textiles in Wearable Uhf Rfid Patch Antennas for Body-Centric Sensing Systems", IEEE Transactions on Antennas and Propagation, vol. 62, No. 12, Dec. 2014, Date of Publication: Oct. 20, 2014, pp. 6454-6462.
Liu et al., "A 10-bit 50-MS/s SAR ADC With a Monotonic Capacitor Switching Procedure", IEEE Journal of Solid-State Circuits, vol. 45, No. 4, Apr. 2010, pp. 731-740.
Lu et al., "Performance evaluation of a long-range RFID tag powered by a vibration energy harvester", IEEE Antennas and Wireless Propagation Letters, vol. 16, 2017, pp. 1832-1835.
Lyu et al., "A 100-M/s 2.6-pJ/pulse compact UWB impulse transmitter based on antenna-and-pulsegenerator codesign", IEICE Electronics Express, vol. 16, No. 24, 2019, 20190672-20190672, 4 pgs.
Lyu et al., "A 915-MHz Far-Field Energy Harvester With—22-dBm Sensitivity and 3-V Output Voltage Based on Antenna-and-Rectifier Codesign", IEEE Microwave and Wireless Components Letters, vol. 29, No. 8, 2019, pp. 557-559.
Marrocco et al., "The art of UHF RFID antenna design: Impedancematching and size-reduction techniques", IEEE Antennas and Propagation Magazine, vol. 50, No. 1, 2008, pp. 66-79.
Nikitin et al., "Power reflection coefficient analysis for complex impedances in RFID tag design", IEEE Transactions on Microwave Theory and Techniques, vol. 53, No. 9, 2005, pp. 2721-2725.
Occhiuzzi et al., "Modeling, design and experimentation of wearable RFID sensor tag", IEEE Transactions on Antennas and Propagation, vol. 58, No. 8, 2010, pp. 2490-2498.
Rahmani et al., "A 1.6mm 3 Wirelessly Powered Reconfigurable FDD Radio with On-Chip Antennas Achieving 4.7 pJ/b TX and 1 pJ/b RX Energy Efficiencies for Medical Implants", Conference Paper, Mar. 2020, DOI: 10.1109/CICC48029.2020.9075935, 5 pgs.
Rahmani et al., "An Integrated Battery-Less Wirelessly Powered RFID Tag with Clock Recovery and Data Transmitter for UWB Localization", Microwave, MTT-S International Symposium, Aug. 4-6, 2020, Los Angeles, CA, USA, pp. 460-463, DOI: 10.1109/IMS30576.2020.9223821.
Rajavi et al., "An energy harvested ultra-low power transceiver for Internet of Medical Things", European Conference on Solid-State Circuits (ESSCIRC): 42nd Solid-State Circuits Conference, Lausanne, Switzerland, Sep. 12-15, 2016, pp. 133-136.

(56) References Cited

OTHER PUBLICATIONS

Riaz et al., "A novel design of UHF RFID passive tag antenna targeting smart cards limited area", 2018 IEEE International Conference on Consumer Electronics (ICCE), 2018, 4 pgs.
Schleircher et al., "IR-UWB radar demonstrator for ultra-fine movement detection and vital-sign monitoring", IEEE transactions on microwave theory and techniques, vol. 61, No. 5, 2013, pp. 2076-2085.
Tan et al., "A 1.2-V 8.3-nJ CMOS humidity sensor for RFID applications", IEEE Journal of Solid-State Circuits, vol. 48, No. 10, 2013, pp. 2469-2477.
Vaz et al., "Full passive UHF tag with a temperature sensor suitable for human body temperature monitoring", IEEE Transactions on Circuits and Systems II: Express Briefs, vol. 57, No. 2, 2010, pp. 95-99.
Wang et al., "Single-antenna Doppler radars using self and mutual injection locking for vital sign detection with random body movement cancellation", IEEE Transactions on Microwave Theory and Techniques, vol. 59, No. 12, 2011, pp. 3577-3587.
Yakovlev et al., "An 11 μW Sub-pJ/bit Reconfigurable Transceiver for mm-Sized Wireless Implants", IEEE Transactions on Biomedical Circuits and Systems, Sep. 2013, vol. 10, No. 1, 4 pgs., DOI:10.1109/CICC.2013.6658501.
Yang et al., "Wearable RFID-enabled sensor nodes for biomedical applications", 58th Electronic Components and Technology Conference, 2008, pp. 2156-2159.
Yeager et al., "A 9 μA, Addressable Gen2 Sensor Tag for Biosignal Acquisition", IEEE Journal of Solid-State Circuits, vol. 45, No. 10, 2010, pp. 2198-2209.

\* cited by examiner

SYSTEMS AND METHODS FOR BATTERY-LESS WIRELESSLY POWERED DIELECTRIC SENSORS

CROSS-REFERENCE TO RELATED APPLICATIONS

The current application is a U.S. national phase of PCT Application No. PCT/US2019/059657 entitled, "Systems and Methods for Battery-Less Wirelessly Powered Dielectric Sensors", filed Nov. 4, 2019, which claims the benefit of and priority under 35 U.S.C. § 119 (e) to U.S. Provisional Patent Application No. 62/820,770 entitled "Systems and Methods for Battery-Less Wirelessly Powered Dielectric Sensors" filed Mar. 19, 2019, and U.S. Provisional Patent Application No. 62/769, 166 entitled "Battery-Less Wirelessly Powered Dielectric Sensor" filed Nov. 19, 2018. The disclosures of PCT Application No. PCT/US2019/059657 and U.S. Provisional Patent Application Nos. 62/820,770 and 62/769, 166 are hereby incorporated by reference in their entirety for all purposes.

STATEMENT OF FEDERALLY SPONSORED RESEARCH

This invention was made with government support under Grant Number 1533688, awarded by the National Science Foundation. The government has certain rights in the invention.

FIELD OF THE INVENTION

The present invention generally relates to wirelessly-powered dielectric sensors with on-chip antennas.

BACKGROUND OF THE INVENTION

Over the past few decades, the number of mobile devices has increased exponentially surpassing the global population. After several generations of evolution, mobile phones now connect more than 4 billion people in the world. In recent years, significant attention is drawn to the Internet of Things (IoT). The next level connectivity extends from mobile phones or tablets to everyday objects, from household appliances to large city infrastructures. With current projections, there will be trillions of small IoT devices distributed in the environment, with sensing, computation and communication capability. To fulfil the goal of trillions of IoT devices, a low-cost IoT node is critical for the advancement of the technology. It is obvious that powering trillions of IoT devices through wire or battery is not practical. Moreover, in certain applications such as bio-implantable device, a simple task such as changing a battery my require significant undertakings including surgery and present significant potential risks and complications that may occur during the in surgery. Furthermore, it would be highly desirable to vastly reduce the size of the bio-implant by removing the need of having a bulky battery within a bio-implant.

SUMMARY OF THE DISCLOSURE

Wirelessly powered dielectric sensors in accordance with various embodiments of the invention are disclosed. In an embodiment, a wirelessly powered dielectric sensor includes: an RF-power receiving antenna that receives electromagnetic power, a power management unit (PMU) including a capacitor to rectify and store the electromagnetic power, and a dielectric constant sensing sensor, where the PMU monitors harvested energy and operates the dielectric sensing sensor, where the dielectric sensing sensor senses a dielectric constant of a material that is in close proximity.

In a further embodiment, the PMU further included a voltage reference circuit, a comparator, a low drop-out (LDO) regulator, where the capacitor is an on-chip storage capacitor.

In still a further embodiment, the PMU monitors a voltage on the capacitor and turns a transmitter circuit on when there is sufficient energy in the capacitor.

In still a further embodiment again, the PMU generates enable signals to turn on the low drop-out regulator to generate a regulated voltage $V_{reg}$ for the dielectric sensing sensor and to turn on the dielectric sensing sensor.

In another additional embodiment, the receiving antenna is an on-chip antenna.

In still another embodiment again, the capacitor is an on-chip capacitor.

In another additional embodiment, the wirelessly powered dielectric sensor further includes a transmitting on-chip antenna, where the transmitting on-chip antenna is used to wirelessly transmit a signal.

In still a further embodiment, the dielectric sensing oscillator drives the transmitting on-chip antenna to radiate back a signal.

In still a further embodiment again, the transmitting on-chip antenna is used to transmit the signal using at least one of a wired communication channel or a wireless communication channel.

In still a further embodiment, the dielectric constant sensing sensor is an oscillator that produces a frequency shift depending on the value of the dielectric constant being measured.

In still a further embodiment again, the PMU operates the dielectric sensing sensor in duty cycle mode.

In still a further embodiment again, the dielectric sensing sensor is used to receive a command where there is a nonconductive isolating layer between a user providing the command and the wirelessly powered dielectric sensor.

In still another additional embodiment, the dielectric sensing sensor includes a metaloxide-metal capacitor (MOMCAP) that provides different capacitance for different materials.

In another embodiment includes a method for wirelessly powering a dielectric sensor, including receiving electromagnetic power using an RF-power receiving antenna, rectifying and storing the electromagnetic power using a capacitor included in a power management unit (PMU), sensing a dielectric constant using a dielectric constant sensing sensor, where the PMU monitors harvested energy and operates the dielectric sensing sensor, where the dielectric sensing sensor senses a dielectric constant of a material that is in close proximity.

In a further embodiment, the PMU further includes a voltage reference circuit, a comparator, a low drop-out (LDO) regulator, wherein the capacitor is an on-chip storage capacitor.

In still a further embodiment, the PMU monitors a voltage on the capacitor and turns a transmitter circuit on when there is sufficient energy in the capacitor.

In still a further embodiment, the PMU generates enable signals to turn on the low drop-out regulator to generate a regulated voltage $V_{reg}$ for the dielectric sensing sensor and to turn on the dielectric sensing sensor.

In still a further embodiment again, the receiving antenna is an on-chip antenna.

In still a further embodiment again, the capacitor is an on-chip capacitor.

In still another embodiment again, the dielectric sensor includes a transmitting on-chip antenna, where the transmitting on-chip antenna is used to wirelessly transmit a signal.

DETAILED DESCRIPTION OF THE DRAWINGS

Figure 1:
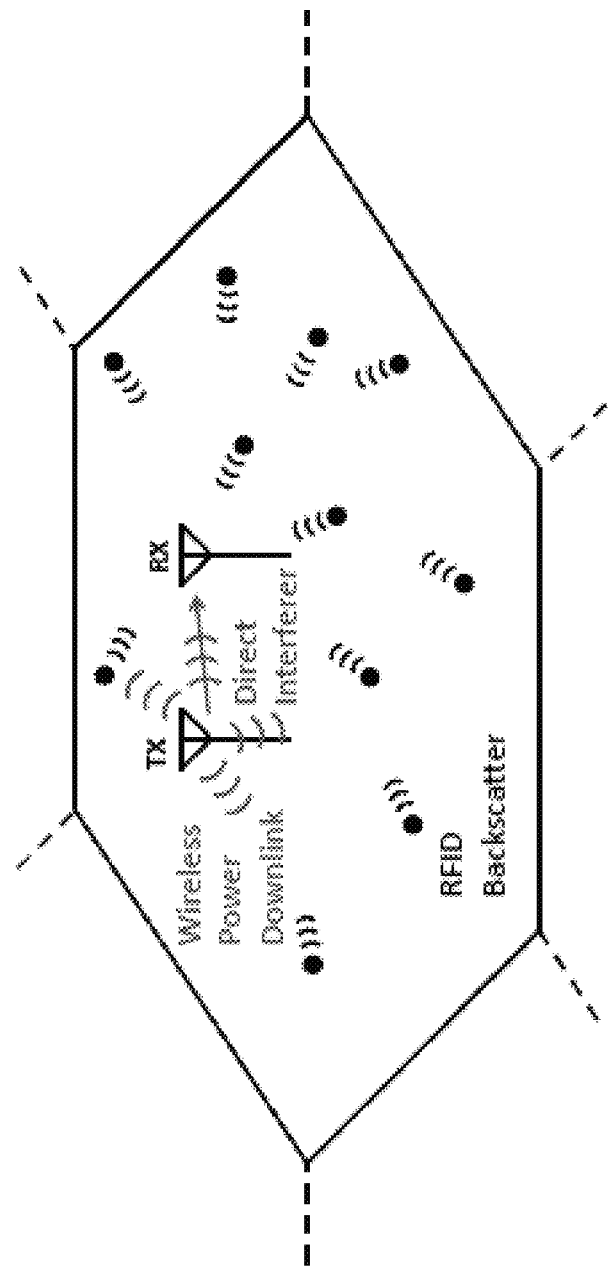
FIG. 1 illustrates self-interference in an RFID system in accordance with several embodiments of the invention.

The internet of things (IoT) has progressed rapidly and providing for the ability to both wirelessly power and communicate with these devices has become essential in furthering the advancement of this technology. Accordingly, many embodiments provide for a wirelessly-powered dielectric sensor. In particular, many embodiments provide a wirelessly powered dielectric sensor microchip fabricated in 180 nm CMOS process for material detection and monitoring. In many embodiments, the dielectric sensor chip includes a receiving and a transmitting antenna, a RF-DC rectifier, a dielectric constant sensing sensor and a power management unit (PMU) that includes a voltage reference circuit, a comparator, a low drop-out regulator (LDO) and on-chip storage capacitor. In many embodiments, the dielectric sensing sensor oscillates at different frequencies depending on a kind of material on top of the sensing capacitor. In several embodiments, the dielectric constant detection is achieved by sensing capacitance change of a capacitor in an oscillator, which causes a shift in the oscillation frequency. In several embodiments, to power the chip, the dielectric sensor chip harvests electromagnetic energy from a continuous-wave source using an on-chip antenna, thus reducing the size of the whole sensor to a millimeter scale. In many embodiments, the dielectric sensor chip radiates back the signal to an external reader antenna. In many embodiments, the dielectric sensor chip may use a frequency division architecture that resolves the conventional self-interference issue in radio frequency ID (RFID) sensors by separating the received and transmitted frequencies.

A dielectric sensor chip in accordance with many embodiments may include applications in 3D gesture sensing for mobile devices, blood sensing in human body implant, oil and gas leakage sensing, hazardous gas sensing among various other fields as appropriate to the requirements of specific applications in accordance with embodiments of the invention. A dielectric sensor chip in accordance with many embodiments may also include applications in medical implants for leak detection, bleeding detection, tumor detection, wound healing, among various other applications.

A dielectric sensor chip in accordance with many embodiments may also include applications in consumer electronics such as smart phones displays and computer displays providing the ability to sense 3D gestures through a touchless interactions of the user with the display, whereby the smart phone is able to sense gestures without a user actually touching the screen or display of the smart phone or other electronic device. In particular, a dielectric sensing may be used to receive commands or users finger gesture where there is a nonconductive isolating layer between the user's finger and the display, for example, a user wearing a glove will still be able to provide commands to the touchscreen of their smart phone. Likewise, a user may not need to actually touch the display of their electronic device with their finger but can have the finger hover above the display to interact with the user interface. Within a 3D gesture sensing context, when a target such as finger or hand presents above a microchip in accordance with various embodiments, the effective dielectric constant of the sensing MOMCAP may be changed, hence the frequency shift can be sensed. The miniaturized sensor chip in accordance with several embodiments can also be utilized in a large array to form a dielectric constant map, which can handle more complex gesture recognition.

A dielectric sensor chip in accordance with many embodiments may also be used in applications within extreme environments where it would be difficult to implement the sensor with wires. For example, a dielectric sensor may be used inside of a high pressure oil or gas pipeline to sense and measure flow properties and send this information to an external receiver. Other applications include, for example, using in oil and gas reservoirs, using within cement to sense whether the cement has cured or not, among various other applications that would benefit from providing sensing capabilities in extreme environments.

In particular, in environment monitoring applications, a wirelessly-powered dielectric sensor in accordance with several embodiments can be used to detect oil or gas leakage along a pipe, measure any one of a variety of variables, including flow, temperature, volume, among various other measurements appropriate to the particular applications, as well as hazardous gas sensing in a lab environment.

As noted above, dielectric sensor chip in accordance with various embodiments can be applied to a human body implant for real-time monitoring such as detecting when a patient is bleeding or detecting a leak in an implant.

A microchip in accordance with various embodiments can be wirelessly powered by RF power from a transmitting antenna. The miniaturized battery-less microchip in accordance with various embodiments can be applied in large amount distributed in the environment. The microchip may detect a target material by measurement of dielectric constant change in the near field (e.g., ~2 cm). As illustrated in FIG. 1, a microchip may include an RF-power receiving on-chip antenna, a rectifier, a power management unit, a dielectric sensing sensor and a transmitting antenna. In certain embodiments, the RF power receiving front-end can be optimized at 9.8 GHz, which can receive continuous rectified DC power of ~100 uW, with a distance of ~4 cm. In several embodiments, the power management unit may monitor the harvested energy and operate the dielectric sensing sensor in duty cycle. In several embodiments, the oscillator may sense the dielectric constant change by a customized 200 um×200 um metal-oxide-metal capacitor (MOMCAP). In certain embodiments, the oscillation free-running frequency may be 4 GHz, and may transmit the signal back to external receiver. The frequency shifts can correspond to kinds of material with different dielectric constant. Many embodiments may map a measured dielectric constant back to possible material in different applications. In certain embodiments, the sensing distance can be 0 to ~2 cm away from the chip. In other embodiments, the sensing distance can be greater than 2 cm away from the chip as appropriate to the requirements of specific applications in accordance with embodiments of the invention.

Figure 2:
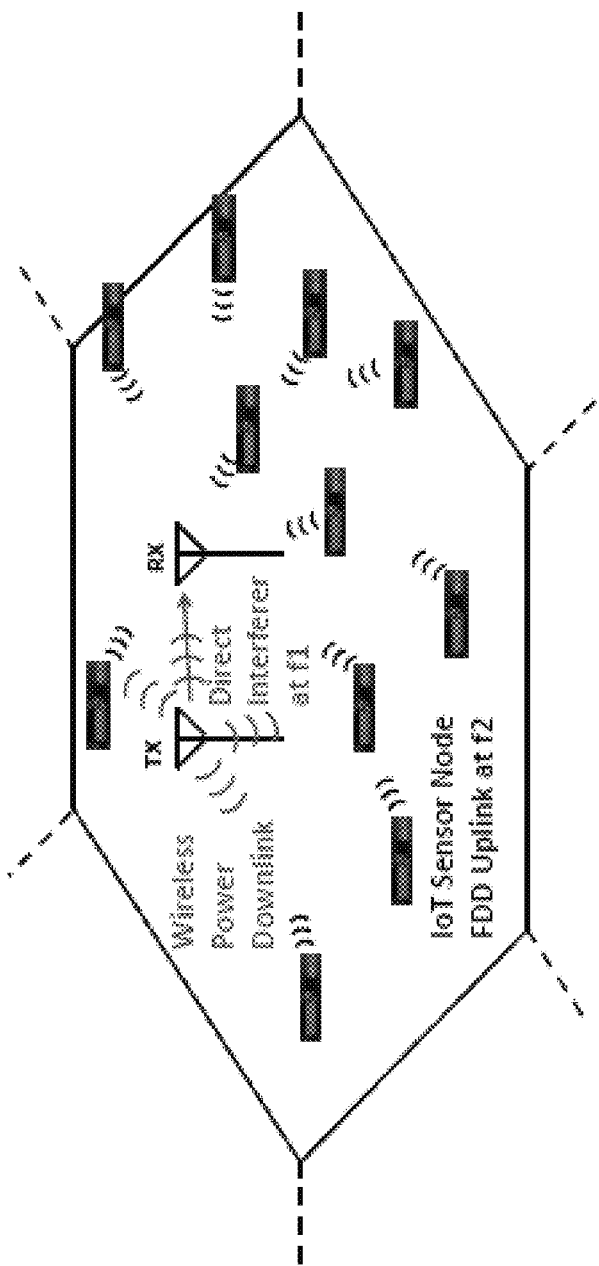
FIG. 2 illustrates a wirelessly powered IoT sensor system with frequency division scheme to solve self-interference in accordance with several embodiments of the invention.
Figure 3:
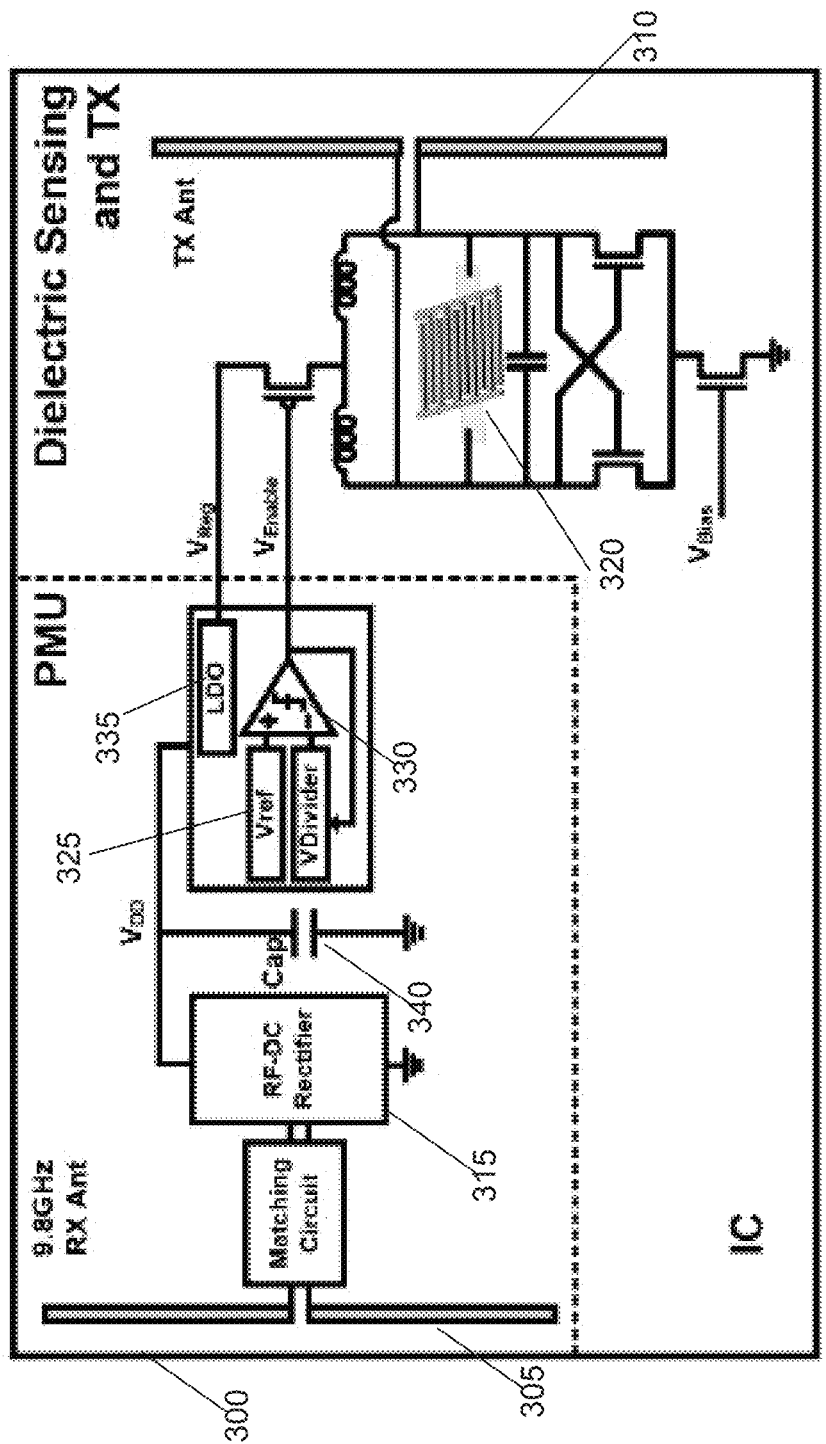
FIG. 3 illustrates a block diagram of a wirelessly-powered dielectric sensor chip in accordance with several embodiments of the invention.

A configuration of wirelessly powered microchip operation in accordance with several embodiments is illustrated in FIG. 2. In many embodiments, the power source may transmit RF power to the microchip sensors. Each microchip can transmit back the signal to a reader. By detecting if the oscillation frequency shifts or not, many embodiments can localize and map the targeted object. A preliminary microchip pixel can be fabricated in 180 nm CMOS process as illustrated in FIG. 3 in accordance with several embodiments of the invention. The microchip can be wirelessly powered, and may send back a signal at a different frequency from 3 GHz to 4 GHz, when there are different materials placed on the top of the chip. The miniaturized microchip may be only 3.9×0.7 mm$^2$ in size.

Accordingly, many embodiments of the invention provide a battery-less mm-sized wirelessly-powered dielectric sensor with on-chip antennas in 180 nm SOI CMOS process. The dielectric constant detection can be achieved by sensing capacitance change of a capacitor in an oscillator, which may cause a shift in the oscillation frequency. In certain embodiments, the chip may harvest electromagnetic energy from a continuous-wave source at 9.8 GHz using an on-chip antenna, which may shrink the whole sensor size to millimeter scale. In several embodiments, the oscillator free-running frequency can be from 3.66 GHz to 4 GHz which may depend on the material on top of the chip. The chip may radiate back the signal to an external reader antenna.

There are several approaches to wirelessly-power a device, such as far-field electromagnetic radiation or near-field inductive coupling, ultrasonic power, thermalelectricity, photovoltaic (PV) or optical power, among various others. Far-field electromagnetic power transfer may be a technique for IoT devices application due to its high power transmission and potential high data rate capacity. Moreover, far-field wireless power transferring at higher frequency in GHz range may allow small antenna size and large range to node size ratio, which greatly benefits IoT device miniaturization. For commercial near-field inductive coupling, it usually may need large external receiving coils, which mainly limits the miniaturization of the sensor node. The operating distance may also be restricted in order to have higher coupling coefficient. Similar miniaturization challenges may also be presented to Radio Frequency Identification (RFID) systems. Conventional RFID sensors typically operate in the sub-gigahertz frequency regime and therefore may require large external antennas with an area exceeding 10 cm^2. This may severely limit the miniaturization of the device and cause complex packaging issues and increased cost. Another challenge is that RFID may apply a backscatter modulation scheme to transmit back signal, leading to a serious self-interference issue. The large power transferring downlink may act as a blocker for uplink backscatter signal. FIG. 1 illustrates receiving a weak reflected signal with an RX antenna, where there can be interference at the same frequency that is coupled from TX to RX, which may greatly degrade the sensitivity and signal-to-noise ratio (SNR) of a reader's receiver. Accordingly, many embodiments of the dielectric sensor chip mitigate the self-interference issue using frequency division to separate downlink and uplink frequency and time division duplexing.

Accordingly, many embodiments provide a wirelessly-powered frequency shift based dielectric sensor. In certain embodiments, the dielectric sensor may harvest power at 9.8 GHz. In order to shrink the size of the entire sensor node, many embodiments integrate the antenna with the energy-harvesting circuits, which may dramatically reduce the overall system size to the millimeter level. In numerous embodiments, the dielectric constant change can be sensed by a customized metal-oxide-metal capacitor (MOMCAP) in the oscillator. The oscillation frequency may change from 3.66

GHz to 4 GHz in the measurement when different materials are placed on the top of the chip. The oscillator may drive another TX on-chip antenna to transmit the signal back. The rectifier front-end and power management unit may also be integrated in accordance with several embodiments of the invention. The whole chip may occupy an area of 2.73 mm² including on-chip antennas.

Described below are architectures of circuits for IoT sensor applications in accordance with many embodiments of the invention. Furthermore, details of circuit designs and optimizations of wireless energy harvesting on-chip antennas and rectifiers, power management units and dielectric sensing sensors in accordance with numerous embodiments are discussed. In many embodiments, the circuit was taped out in a 180 nm SOI CMOS process and tested.

System Architecture

In many embodiments, in order to minimize the self-interference issue, a frequency division duplexing scheme may be adopted. FIG. 2 illustrates a wirelessly powered IoT sensor system with frequency division scheme to solve self-interference issue in accordance with several embodiments of the invention.

As illustrated in FIG. 2, the IoT sensor node's transmitted frequency can be set at frequency f2, which may be different than the signal received at frequency f1 from the base station transmitter. This frequency division may eliminate the self-interference and increases the dynamic range of the receiver at the reader. Although FIG. 2 illustrates a particular wirelessly powered IoT sensor system with a frequency division scheme, any of a variety of frequency division schemes may be utilized as appropriate to the requirements of specific applications in accordance with embodiments of the invention.

A dielectric sensor chip may include circuitry for both wirelessly powering the chip and circuitry for sensing and transmitting a signal to a receiver antenna. FIG. 3 illustrates a block diagram of a wirelessly-powered dielectric sensor node in accordance with several embodiments of the invention. As illustrated, the dielectric sensor chip 300 may include a receiving on-chip dipole antenna 305 and a transmitting on-chip dipole antenna 310, a RF-DC rectifier 315, a frequency-shift dielectric constant sensing sensor 320 and a power management unit (PMU) which can include a voltage reference circuit 325, a comparator 330, a low drop-out regulator (LDO) 335, an on-chip storage capacitor 340.

The on-chip antenna may receive the incoming electromagnetic power and may feed it to the matching circuit and energy harvesting rectifier. The power may be rectified and stored in an on-chip capacitor. The PMU unit may continuously monitor the voltage on the storage capacitor and may turn the transmitter circuit on after the chip scavenges and stores sufficient energy in the storage capacitor. In several embodiments, when the voltage on the storage capacitor ($V_{DD}$) reaches a particular threshold, such as for example 1.6 V ($V_{High}$) in certain embodiments, the PMU may generate enable signals ($\overline{V_{Enable}}$), to turn on the low drop-out regulator to generate a regulated voltage ($V_{Reg}$) for oscillator. The PMU also may turn on the dielectric sensing oscillator, which may oscillate at frequency from a particular range, for example 3.66 GHz to 4 GHz in certain embodiments, depending on the kind of material on top of the sensing capacitor. In many embodiments, the oscillator may drive the TX on-chip antenna and radiate back the signal. This event may discharge the storage capacitor. In several embodiments, when the capacitor voltage drops to a particular threshold, for example 1.2 V ($V_{Low}$), the PMU turns the oscillator off and the chip enters the sleep mode. Although FIG. 3 illustrates a particular circuit architecture of a wirelessly-powered dielectric sensor chip, any of a variety of circuit architectures may be utilized as appropriate to the requirements of specific applications in accordance with embodiments of the invention.

Figure 4:
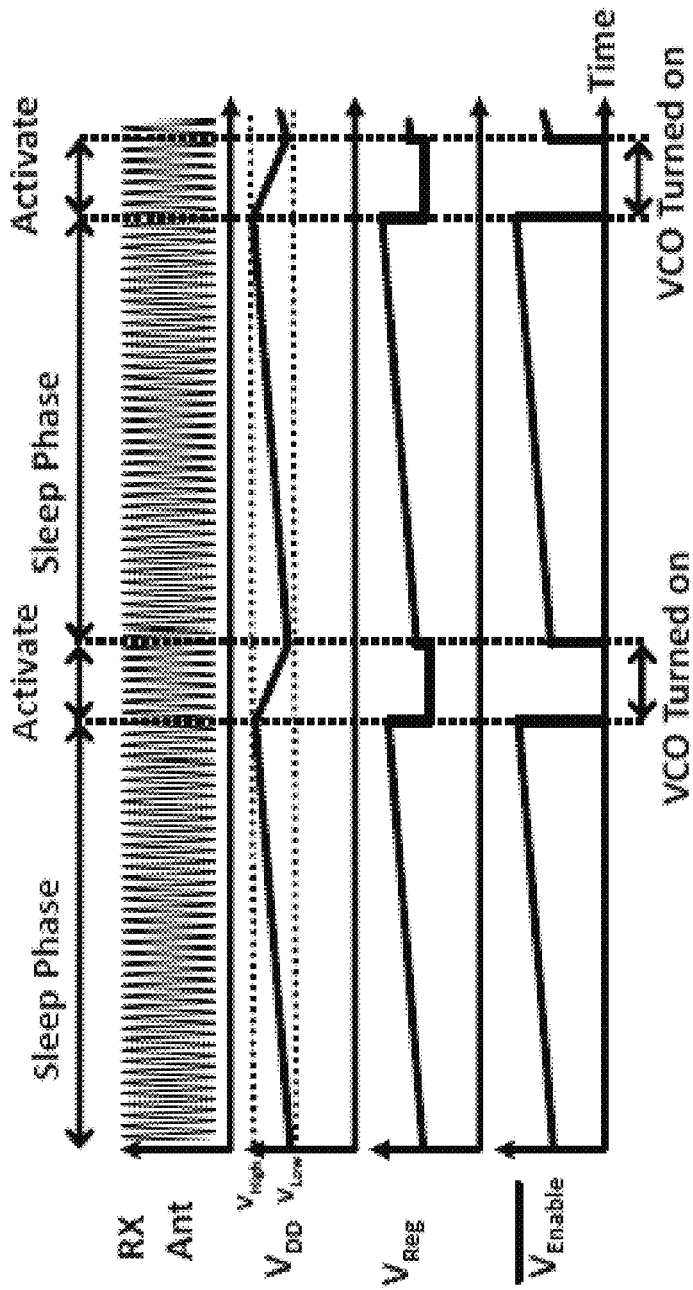
FIG. 4 illustrates a transient diagram of voltages in duty-cycled operation in accordance with several embodiments of the invention.

FIG. 4 illustrates a timing diagram of a duty-cycled operation in accordance with various embodiments of the invention. Applying duty-cycled operation may allow higher power consumption of the oscillator, while low wireless power can be harvested.

Circuit Design and Optimization of RF Powered Dielectric Sensor

Discussed below are RX on-chip antenna designs that may be utilized within dielectric sensor chips together with rectifiers in accordance with several embodiments of the invention. Many embodiments may choose the power downlink frequency to achieve an optimum total power conversion efficiency, where maximum DC power is rectified at output storage capacitor when fixing the RF source power and the distance between the source and the receiver front-end. Then, the power management circuit may be designed to operate the sensor node in duty cycle mode in accordance with numerous embodiments. Finally, a dielectric sensing capacitor and oscillator may be simulated and analyzed.

RF Rectifier Antenna Co-Design and Frequency Optimization

Figure 5:
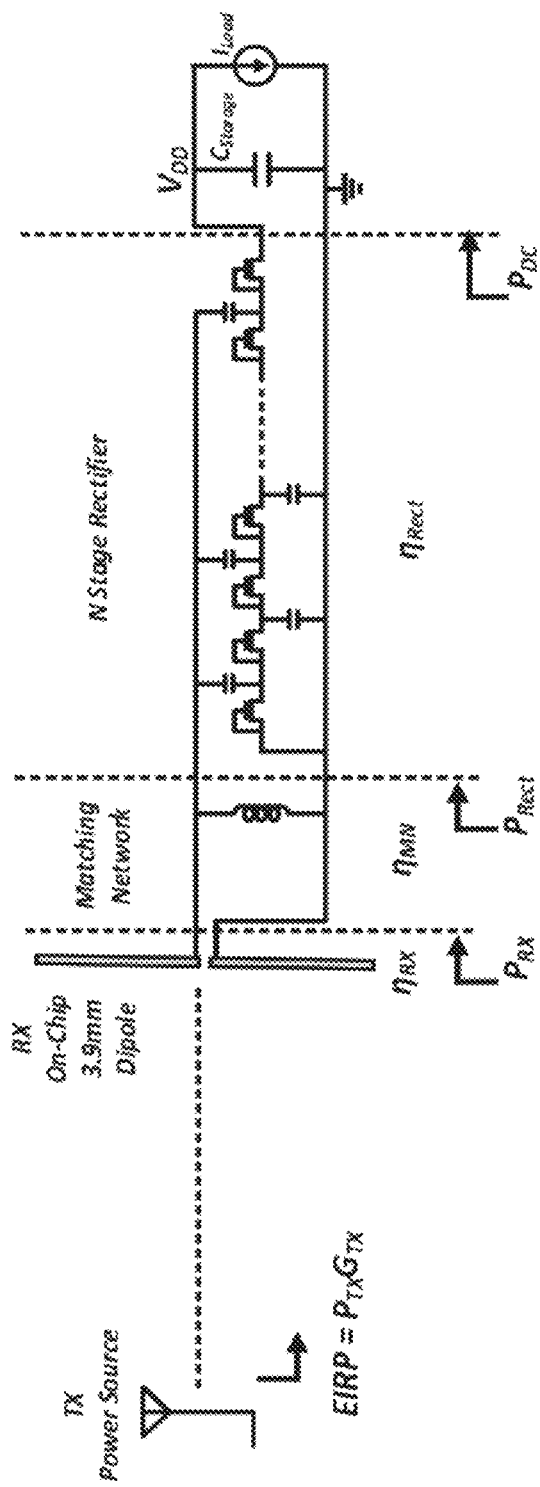
FIG. 5 illustrates wirelessly powered harvesting scheme, with TX antenna and power receiving front-end: RX antenna, matching circuit, and rectifier in accordance with several embodiments of the invention.

Many embodiments provide for the wireless powering of the dielectric sensors. FIG. 5 illustrates a wirelessly powered harvesting scheme, with TX antenna and power receiving front-end: RX antenna, matching circuit, and rectifier in accordance with several embodiments of the invention.

For a common RF power front-end structure as shown in FIG. 5, a maximum converted DC power at the rectifier output may be desired. The converted DC power ($P_{DC}$) may be a function of the received power from the antenna ($P_{RX}$), matching network circuit efficiency ($\eta MN$), and rectifier conversion efficiency ($\eta Rect$).

$$P_{DC} = P_{RX} \eta_m \eta_c \quad (1)$$

The receiver antenna's received power can be depicted by the Friis equation:

$$P_{RX} = \frac{P_{TX} G_{TX}}{4\pi d^2} \frac{G_{RX} \lambda^2}{4\pi} = \frac{EIRP_{TX}}{4\pi d^2} \frac{\eta_{RX} D_{RX} \lambda^2}{4\pi} \quad (2)$$

where $P_T$, $G_{TX}$, $EIRP_{TX}$ are transmitting power, gain and equivalent isotropically radiated power of the transmitting antenna respectively, $\lambda$ is the wavelength, $G_{RX}$ is the gain of the receiving antenna, d is the distance between TX and RX, $D_{RX}$ is the directivity of the receiver antenna. $\eta RX$ is the radiation efficiency of receiving antenna. The matching circuit efficiency may be defined as:

$$\eta_{MN} = \frac{P_{Rect}}{P_{RX}} \quad (3)$$

where $P_{Rect}$ is the power delivered to the rectifier input. While the rectifier conversion efficiency can be defined as:

$$\eta_{Rect} = \frac{P_{DC}}{P_{Rect}} \qquad (4)$$

Many embodiments investigate into each of the three stages and optimize the operating frequency in order to get the most rectified DC power to the storage capacitor.

Receiver Antenna

Figure 6:
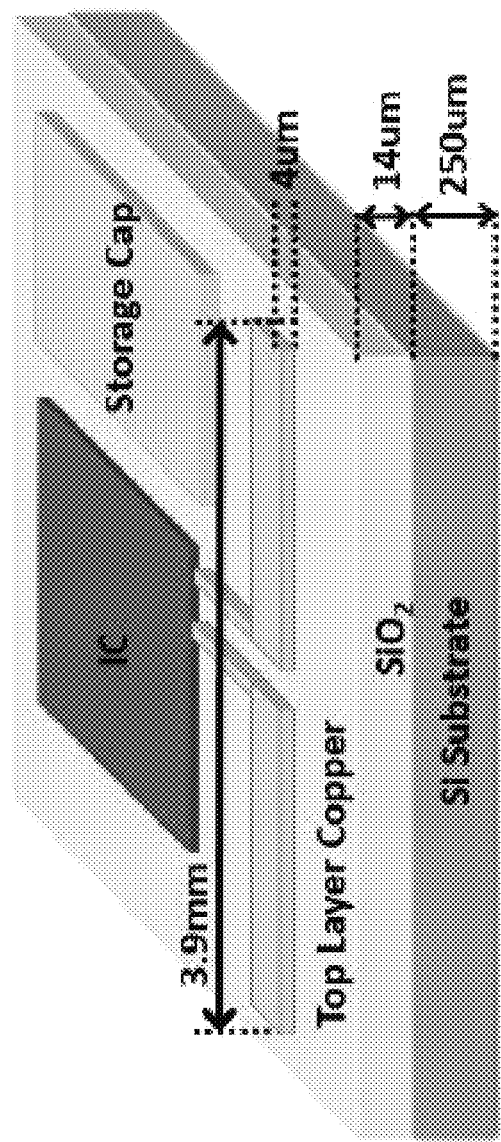
FIG. 6 illustrates on-chip dipole antenna structure EM simulation in HyperLynx 3D EM in accordance with several embodiments of the invention.

In order to miniaturize the size of a sensor node, many embodiments of the dielectric sensor chip may integrate one or more on-chip antennas. Due to the limited die dimension, in many embodiments, the on-chip receiving antenna may be implemented as a dipole antenna. In certain embodiments, the dipole antenna may have a length of 3.9 mm. The received power may suffer from the trade-off of path loss and radiation efficiency. As frequency becomes higher and closer to its resonant frequency, the power link may have more path loss but benefit from a greater radiation efficiency of the receiving antenna. In several embodiments, the antenna may be implemented on a 250-m thick silicon substrate and a 14-m thick silicon dioxide layer. FIG. 6 illustrates an antenna implemented on a 250-m thick silicon substrate and a 14-m thick silicone dioxide layer in accordance with a particular embodiment of the invention. An EM simulation of this structure by Hyperlynx 3D EM was done to characterize the on-chip dipole antenna. Although FIG. 6 illustrates a particular di-pole antenna design, any of a variety of antenna designs at different sizes may be implemented as appropriate to the requirements of specific applications in accordance with embodiments of the invention.

Figure 7:
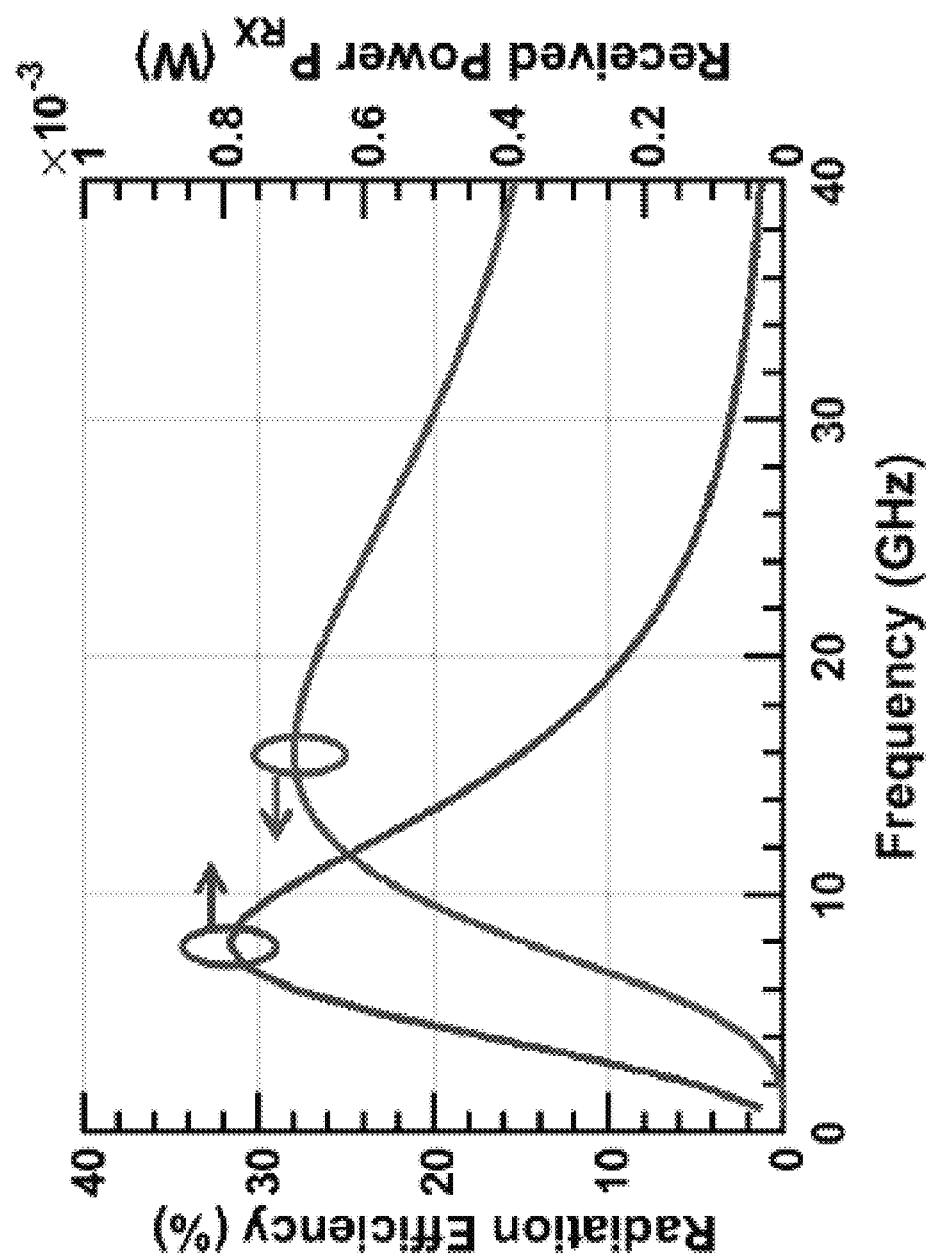
FIG. 7 illustrates on-chip dipole antenna radiation efficiency versus frequency in accordance with several embodiments of the invention.

FIG. 7 illustrates a simulated radiation efficiency in accordance with an embodiment of the invention. In certain embodiments, the dipole antenna may achieve a maximum radiation efficiency of 28% at 17 GHz. In 180 nm SOI CMOS process, the silicon substrate can have a conductivity of only 0.1 S/m. Due to this low substrate loss, the radiation efficiency is not degraded too much.

Figure 8:
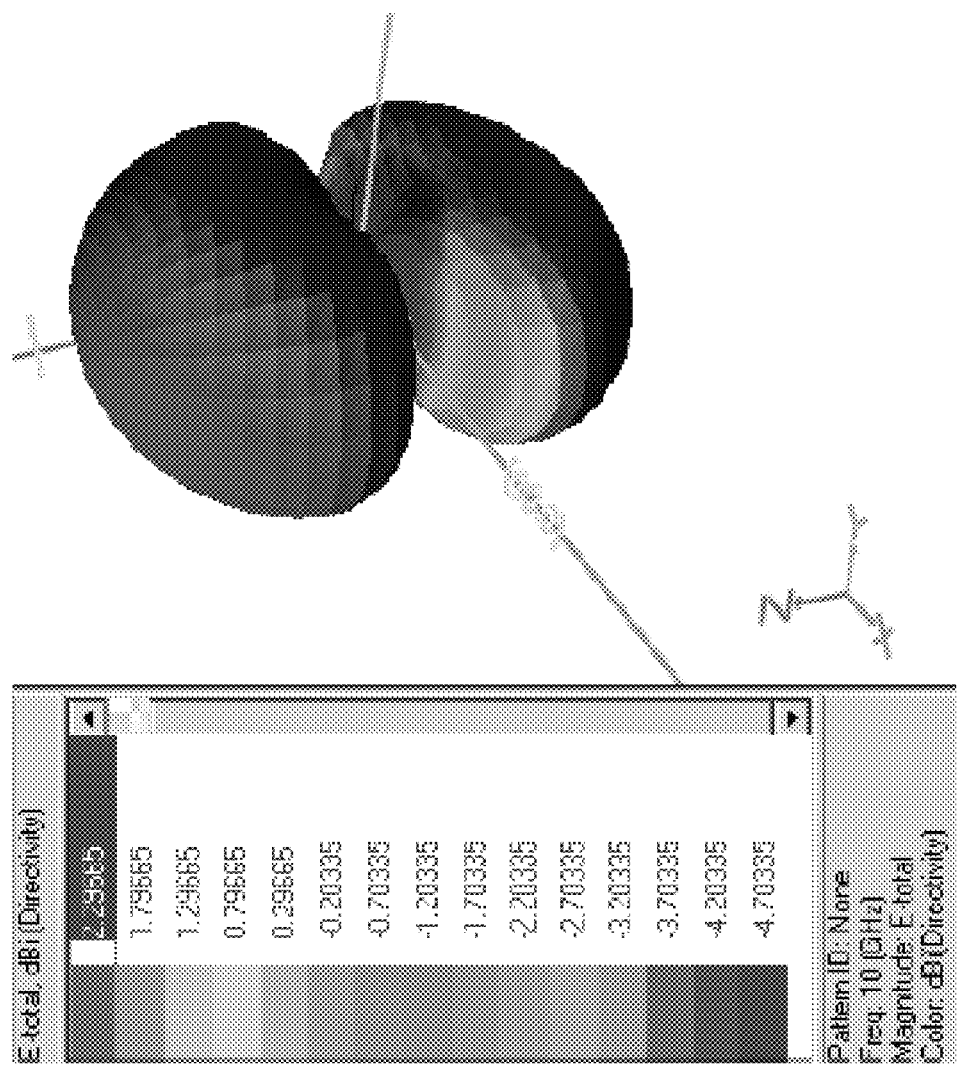
FIG. 8 illustrates radiation pattern of on-chip RX antenna directivity at 10 GHz in accordance with several embodiments of the invention.
Figure 9:
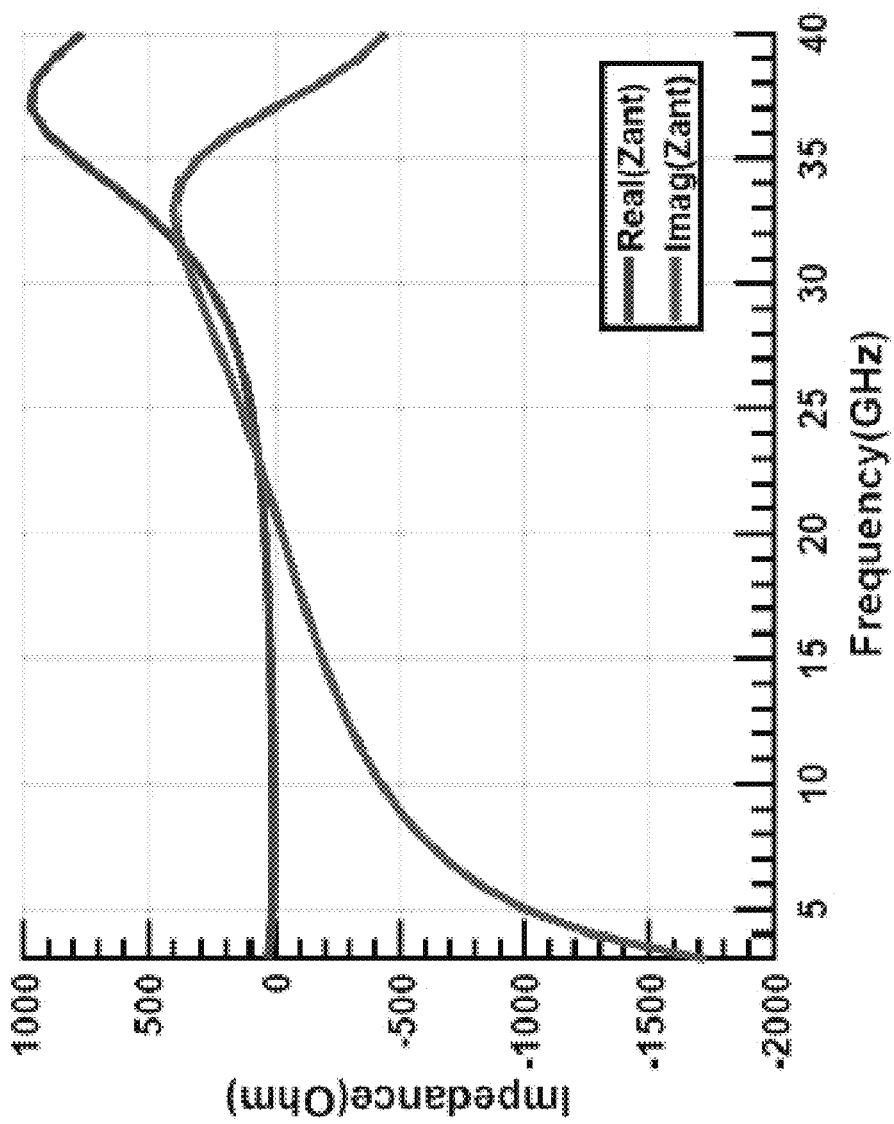
FIG. 9 illustrates on-chip dipole antenna impedance versus frequency in accordance with several embodiments of the invention.

In the case where EIRP of the transmitter antenna is 1 W and the distance between the TX and the sensor node is 5 cm, the received power is shown in FIG. 7. After taking into account of the path loss, the maximum point can be shifted to around 8 GHz. A 3D radiation pattern of the antenna directivity at 10 GHz in accordance with several embodiments is illustrated in FIG. 8, with a maximum directivity of 2.2 dBi. The dipole antenna impedance in accordance with several embodiments is shown in FIG. 9. The quality factor of the antenna may play an important role in matching efficiency which is described below. Further details for designing RF wireless power receiving on-chip antennas as related to FIGS. 3, 5, 6, and 14 can be found in Pozar, David M. "Microwave engineering" John Wiley & Sons, 2009, Chapter 14, "Introduction to Microwave Systems", starting on page 658, and in Balanis, Constantine A. "Antenna theory: analysis and design", John Wiley & sons, 2016, Chapter 2, "Fundamental Parameters of Antennas" starting on page 27 and Chapter 4 "Linear Wire Antennas" starting on page 151, and in Rahmat-Samii, Yahya, and Jaehoon Kim. "Implanted antennas in medical wireless communications." Synthesis Lectures on Antennas 1.1 (2005): 1-82. the disclosures of which are hereby incorporated by reference herein in their entirety.

Matching Circuit

Figure 10:
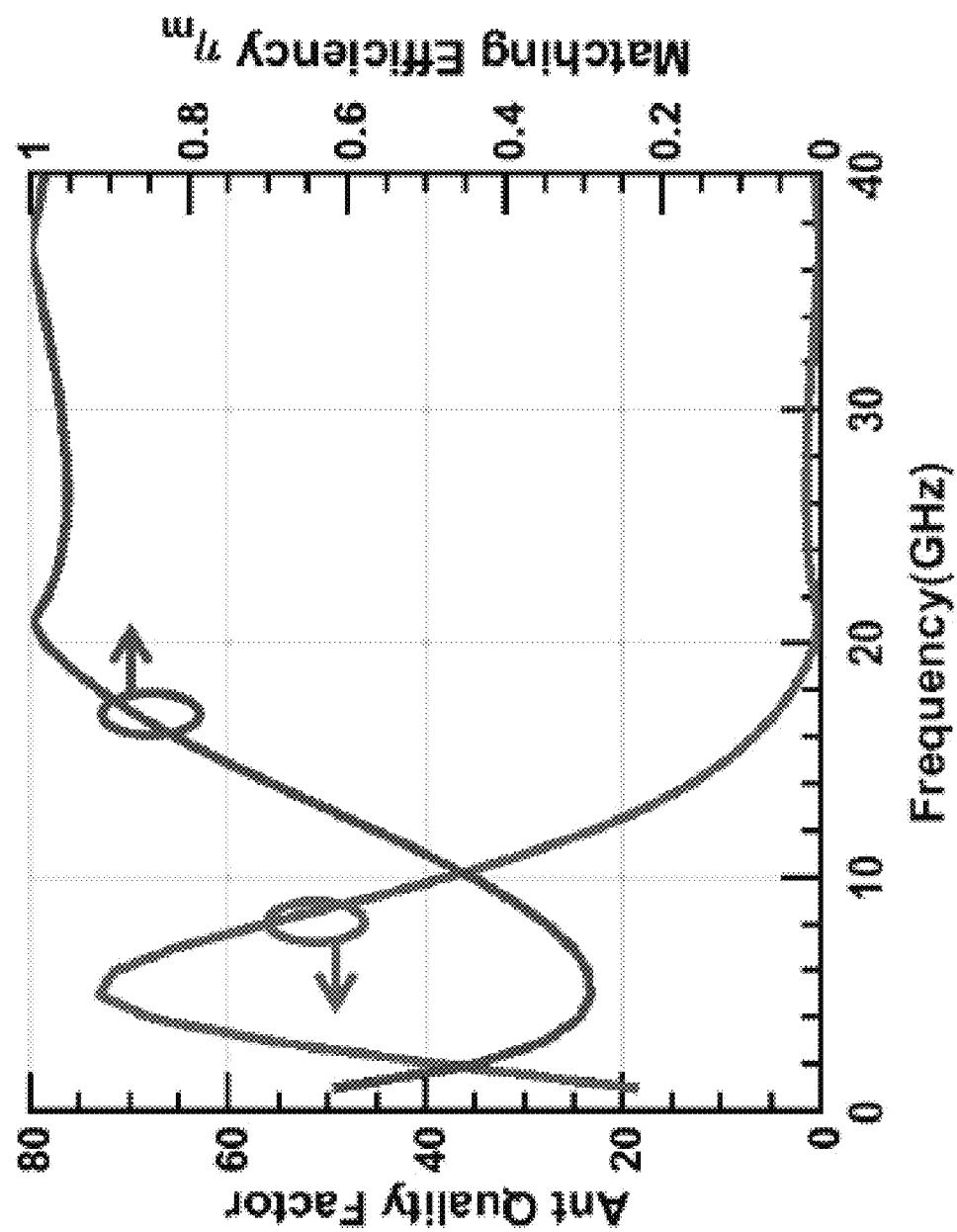
FIG. 10 illustrates antenna quality factor and matching circuit efficiency versus frequency in accordance with several embodiments of the invention.

In many embodiments of the dielectric sensor, a single L matching topology may be used, due to its simplicity. Also, more complex matching topologies such as π-matching or T-matching, with more lossy on-chip passive components may cause lower efficiency. Due to the lossy component in matching network, matching efficiency can usually not be maximized at conjugate match between RX antenna and rectifier. Based on equation 5 and 6 below, the matching circuit efficiency ($\eta_m$) can be a function of the quality factor of the matching component and the quality factor of the receiver antenna. In simulation, certain embodiments fix the matching component quality factor as 15, and based on the simulated on-chip dipole antenna impedance and quality factor, the matching efficiency is plotted in FIG. 10 in accordance with several embodiments. In certain embodiments, a frequency around dipole's half wavelength resonance frequency 21 GHz is preferable, where the receiver antenna quality factor is small.

$$\eta_m = \frac{Q_C^2 + 1}{Q_C^2 + Q_C Q_A}, \text{ when } Q_A > \frac{2Q_C}{Q_C^2 - 1} \qquad (5)$$

$$\eta_m = \frac{2}{1 + \sqrt{1 + Q_A^2}}, \text{ when } Q_A < \frac{2Q_C}{Q_C^2 - 1} \qquad (6)$$

Rectifier

Figure 12:
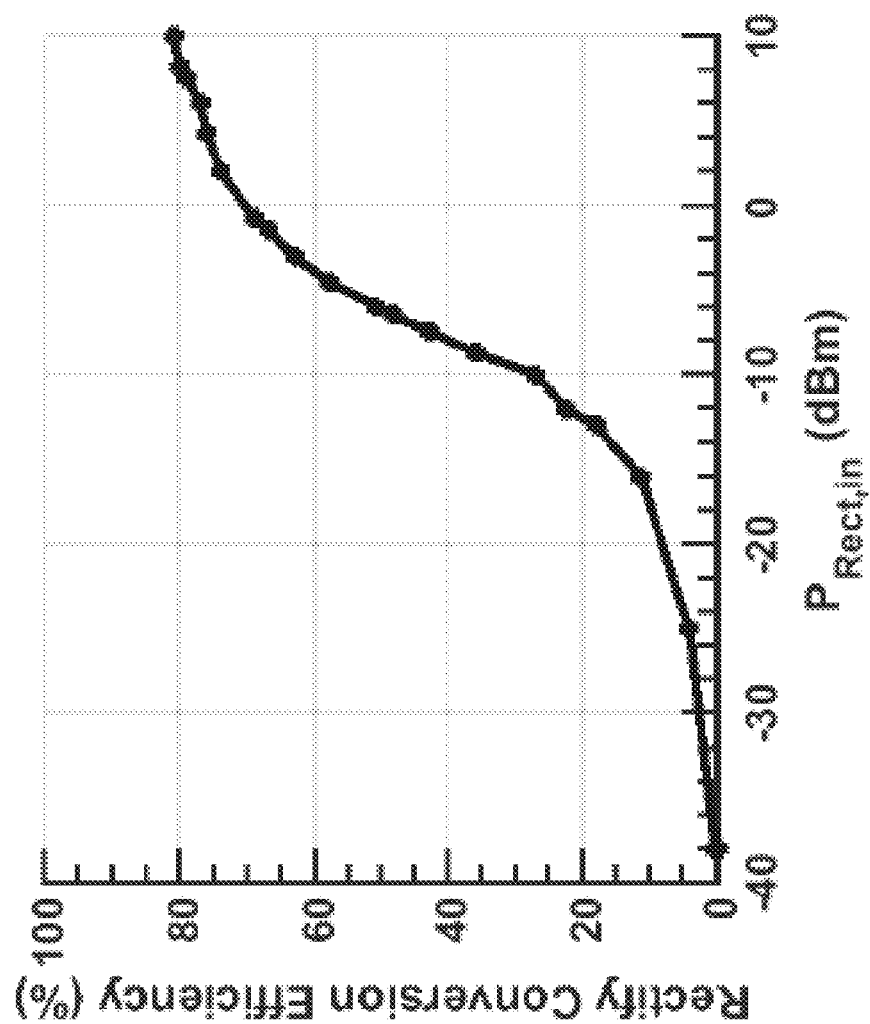
FIG. 12 illustrates rectifier conversion efficiency versus rectifier input power in accordance with several embodiments of the invention.

Many embodiments of the dielectric sensor chip may include a rectifier. The rectifier in accordance with several embodiments may be implemented as multiple-stage Dickson rectifier. The conversion efficiency of the rectifier may be a weak function of frequency in the operating frequency band. However, conversion efficiency can be a strong function of input power. The conversion efficiency of a ten-stage Dickson rectifier versus input power at 10 GHz is simulated and plotted in FIG. 12 in accordance with several embodiments of the invention.

Figure 11:
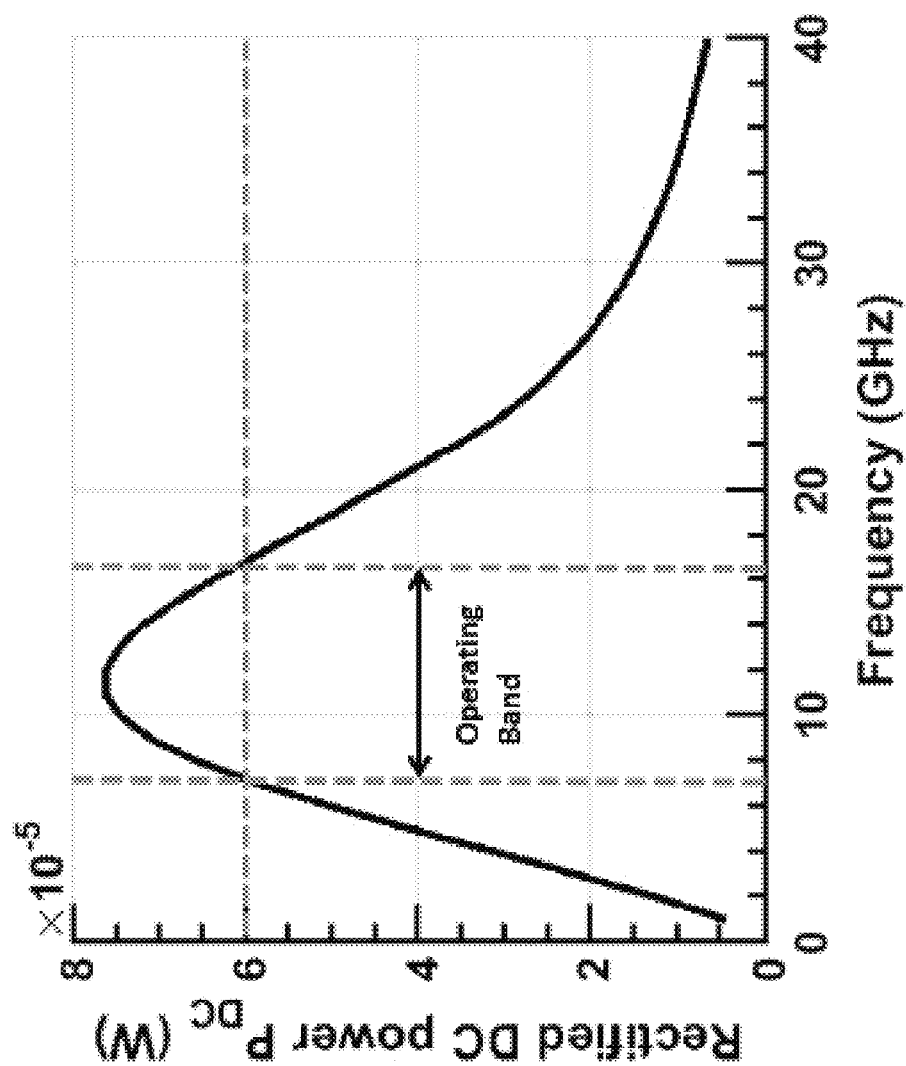
FIG. 11 illustrates overall DC output power at rectifier output versus frequency in accordance with several embodiments of the invention.

Considering all three of these stages, the overall DC output power at the rectifier output versus frequency is shown in FIG. 11 in accordance with an embodiment of the invention. As a trade off a path loss, RX radiation efficiency and matching efficiency, the optimum operating frequency band may be around 10 GHz.

Based on the optimum operating frequency, a ten-stage Dickson rectifier can be implemented. A 3.4 nH inductor may be used at the input to resonate with the dipole antenna and maximize the amplitude of the input voltage. In several embodiments, to achieve a DC voltage of 1 V on a 1.1 nF MIM storage capacitor, a minimum received power of −16.1 dBm may be used. At this input power level, a conversion efficiency of 7% at 10 GHz can be achieved.

Power Management Unit

In several embodiments of the dielectric sensor, because there may be a gap between the μW level of the harvested power and the mW level of the oscillator's power consumption, a power management unit (PMU) may be needed to monitor the supply voltage and operate the oscillator in duty cycles.

In many embodiments, the PMU can be composed of a voltage reference, a comparator, a divider, and a low dropout regulator (LDO). In several embodiments, first, in the sleep mode, the PMU turns off the oscillator. The voltage reference circuit may generate a reference voltage, for example $V_{ref}$ of 0.25 V, while the voltage divider chain generates the voltage, $V_{div}$, which may be a ratio of the $V_{DD}$. Slowly, the storage capacitor can be charged. When $V_{DD}$ reaches a high threshold, for example of 1.6 V, and the $V_{div}$ becomes greater than $V_{ref}$, the comparator may generate an active output enable signal ($\overrightarrow{V_{Enable}}$). The enable signal may positively feed back to the voltage divider, leading to a larger dividing ratio and $V_{div}$, which further switches on the enable signal. The enable signals may turn on the oscillator and low-dropout regulator that generates a particular, e.g. 1 V, regulated supply voltage. Subsequently in the work mode, the oscillator may quickly discharge storage capacitor and $V_{DD}$ drops. When $V_{DD}$ reaches to a lower threshold, e.g. of 1.2 V, and $V_{div}$ becomes smaller than $V_{ref}$, the enable signals may be switched off. The oscillator and LDO may revert back to sleep mode.

Figure 13:
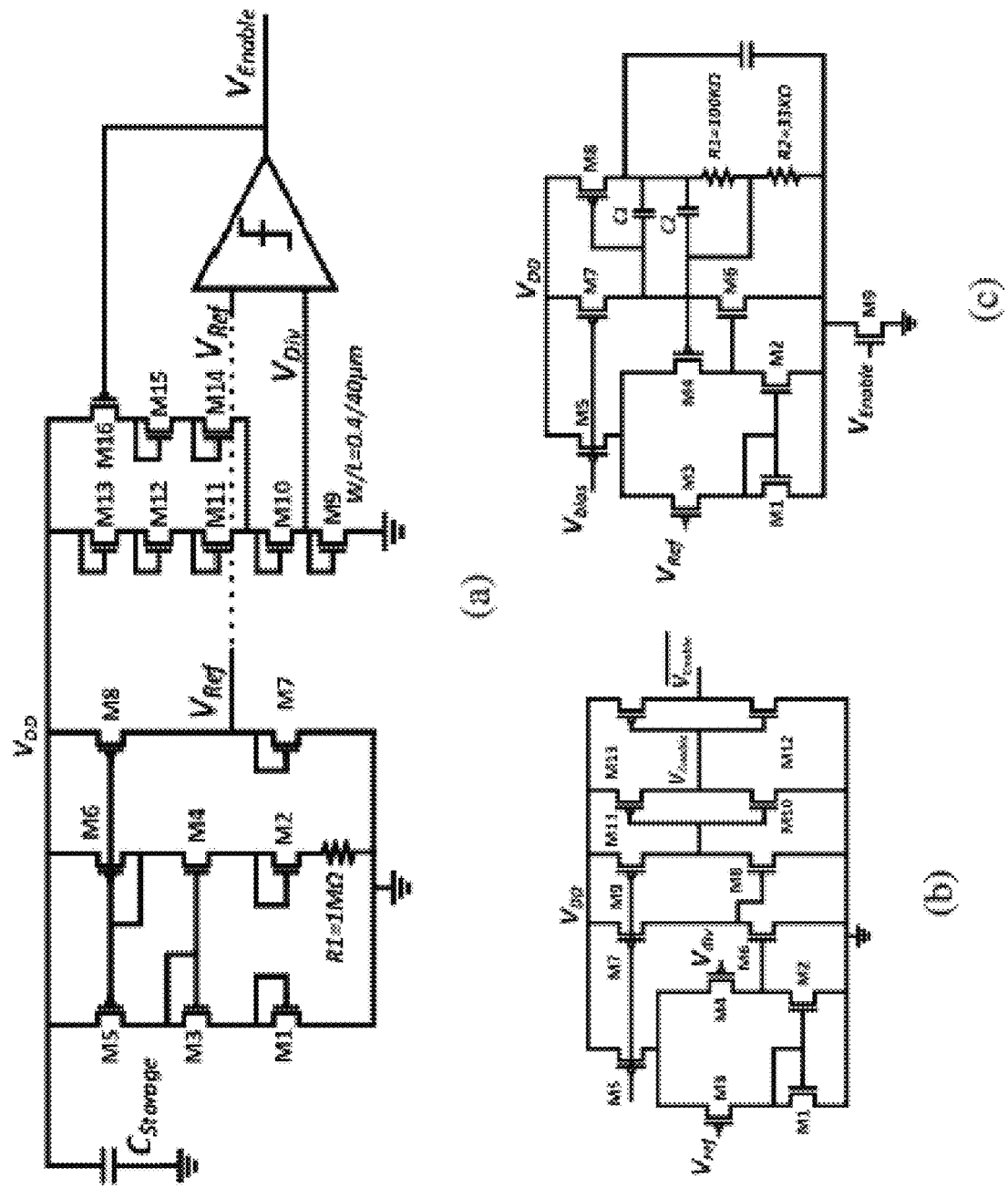
FIG. 13a illustrates schematics of voltage reference and voltage divider in accordance with several embodiments of the invention.
FIG. 13b illustrates schematics of comparator in accordance with several embodiments of the invention.
FIG. 13c illustrates schematics of LDO in accordance with several embodiments of the invention.

In many embodiments, the voltage reference may operate in a subthreshold region. Based on the relation that current following through M1 M2 transistor may have an exponential relation with its $V_{gs}$, the voltage on resistor R1 may be only a function of transistor size ratio, which can be independent of $V_{DD}$ voltage. In a voltage divider, the diode connected transistor can be set to have a small W/L ratio to gain a large equivalent resistance, thus reducing the power consumption. In several embodiments, the LDO may be implemented with a two stage error amplifier. Compensation can be achieved with capacitor C1 and C2. In certain embodiments, the LDO's power consumption can be 22 µW, but it may be only awake when the oscillator is turned on. In certain embodiments, its leakage current can be only 300 pA when in sleep mode, which is negligible to the power consumption of other PMU circuits. The schematics of each block are shown in FIG. 13 in accordance with several embodiments of the invention. In particular, FIG. 13 block (a) illustrates a schematics of a voltage reference and voltage divider, FIG. 13 block (b) illustrates a schematics of a comparator and FIG. 13 block (c) illustrates schematics of an LDO. Although FIG. 13 illustrates a particular schematics for a voltage reference and voltage divider, a comparator, and an LDO, any of a variety of schematics and circuit architectures may be utilized as appropriate to the requirements of specific applications in accordance with embodiments of the invention.

The power consumption of the each block, including the voltage reference, voltage divider and comparator illustrated in FIG. 13 is shown in Table I below. In certain embodiments, the total power consumption in sleep mode is less than 200 nA, when $V_{DD}$ is 1 V.

TABLE I

Current Consumption

| | Current Consumption in Sleep Mode |
|---|---|
| Voltage Reference | 43 nA |
| Voltage Divider | 5 nA |
| Comparator | 110 nA |

Dielectric Sensing sensor

Figure 14A:
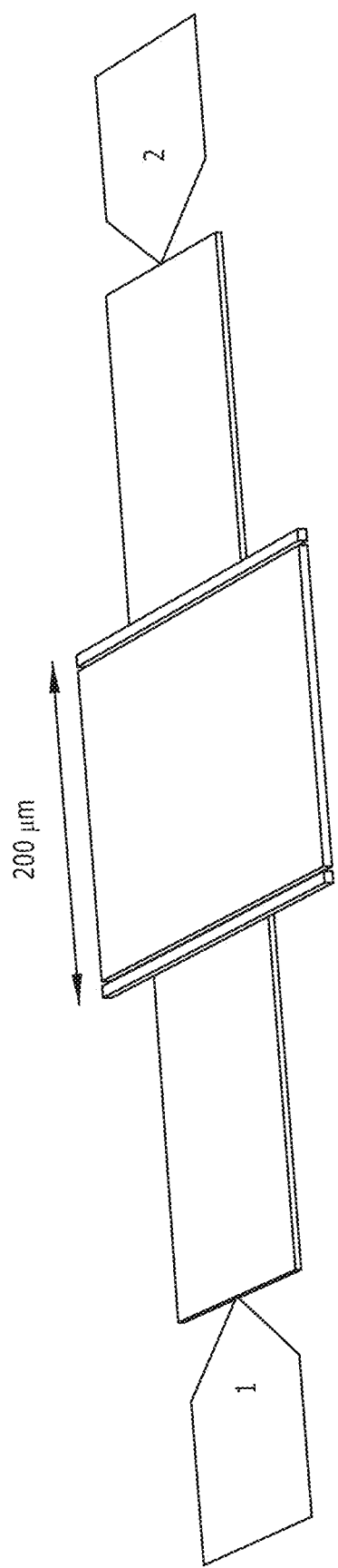
FIG. 14a illustrates MOMCAP structure in 180 nm CMOS top metal layer in accordance with several embodiments of the invention.
Figure 14B:
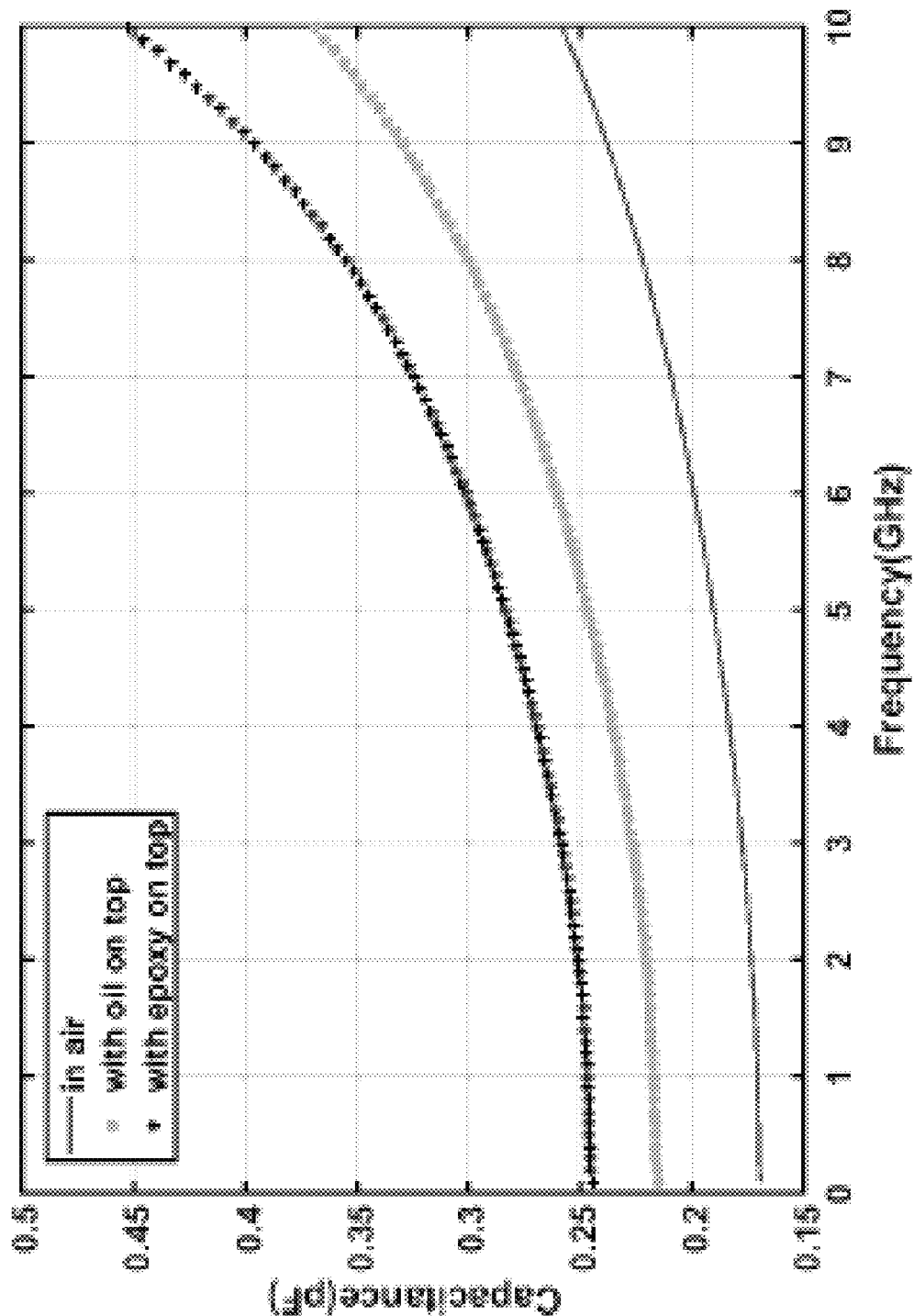
FIG. 14b illustrates capacitance with oil and epoxy on top, versus frequency in accordance with several embodiments of the invention.

In many embodiments, the dielectric sensing can be performed by a customized metaloxide-metal capacitor (MOMCAP) which may be implemented using the top metal layer in this process. FIG. 14a illustrates a MOMCAP structure in 180 nm CMOS top layer in accordance with an embodiment of the invention. The MOMCAP may present different capacitance with the different target material on its top. A LC cross-coupled pair oscillator can be designed utilizing the MOMCAP in resonant tank, which translates the capacitance into oscillation frequency. The oscillator may drive another on-chip dipole antenna to transmit this signal back to external receiver.

Figure 14C:
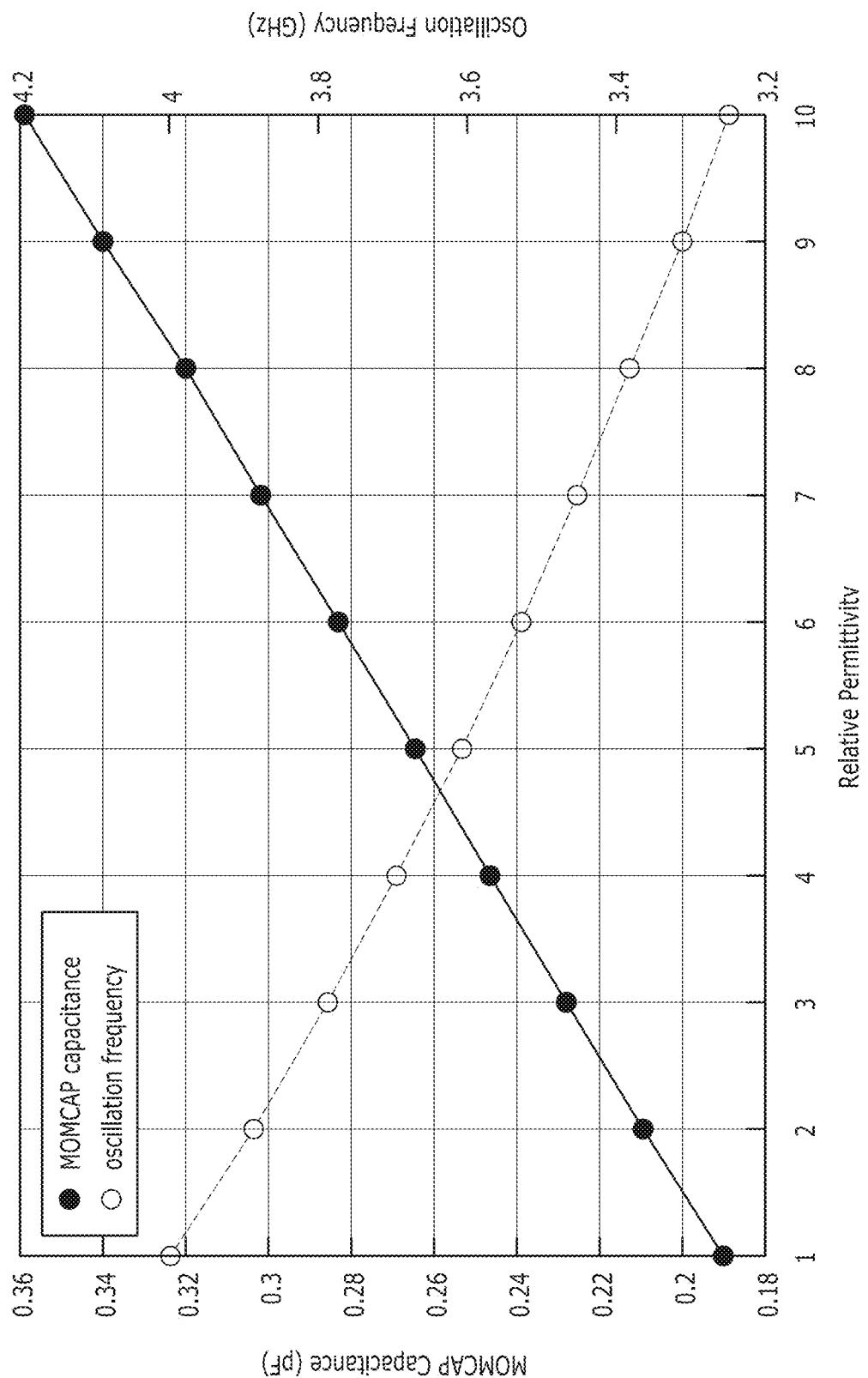
FIG. 14c illustrates capacitance and oscillation frequency versus dielectric constant of material on top in accordance with several embodiments of the invention.

In many embodiments, the MOMCAP size can be 200 by 200 µm, including 10 fingers on each side, with a finger width and gap distance of 5 µm. The silicon substrate thickness may be 250 µm, with a 14 µm silicon dioxide on top. The passivation layer above the MOMCAP may be removed to improve the sensitivity to the change in the dielectric constant of the material placed on the chip. The MOMCAP capacitance can be simulated in EM simulator Hyperlynx 3DEM is about 184 fF when the chip is placed in air as illustrated in FIG. 14a in accordance with several embodiments of the invention. The effective capacitance may increase if a high dielectric constant material is placed top of MOMCAP, causing a lower oscillation frequency. In certain embodiments, the oscillation frequency may be set at 4 GHz when the dielectric sensor chip is placed in the air. The oscillator may consume 4 mW during oscillation. The capacitance of MOMCAP with olive oil (dielectric constant of 3.1) and epoxy (dielectric constant of 5) on top are also simulated and reported in FIG. 14b in accordance with several embodiments of the invention. FIG. 14c illustrates that as dielectric constant increases, the MOMCAP capacitance may increase leading to a smaller oscillation frequency in accordance with several embodiments of the invention. In certain embodiments, the oscillator may directly drive another on-chip dipole antenna at around 4 GHz. The antenna radiation efficiency can be 4% at 4 GHz. Although FIG. 14a illustrates a particular MOMCAP structure and size fabricated in 180 nm CMOS top metal layer, any of a variety of structures, sizes, and fabrication processes may be utilized as appropriate to the requirements of specific applications in accordance with embodiments of the invention.

Figure 15:
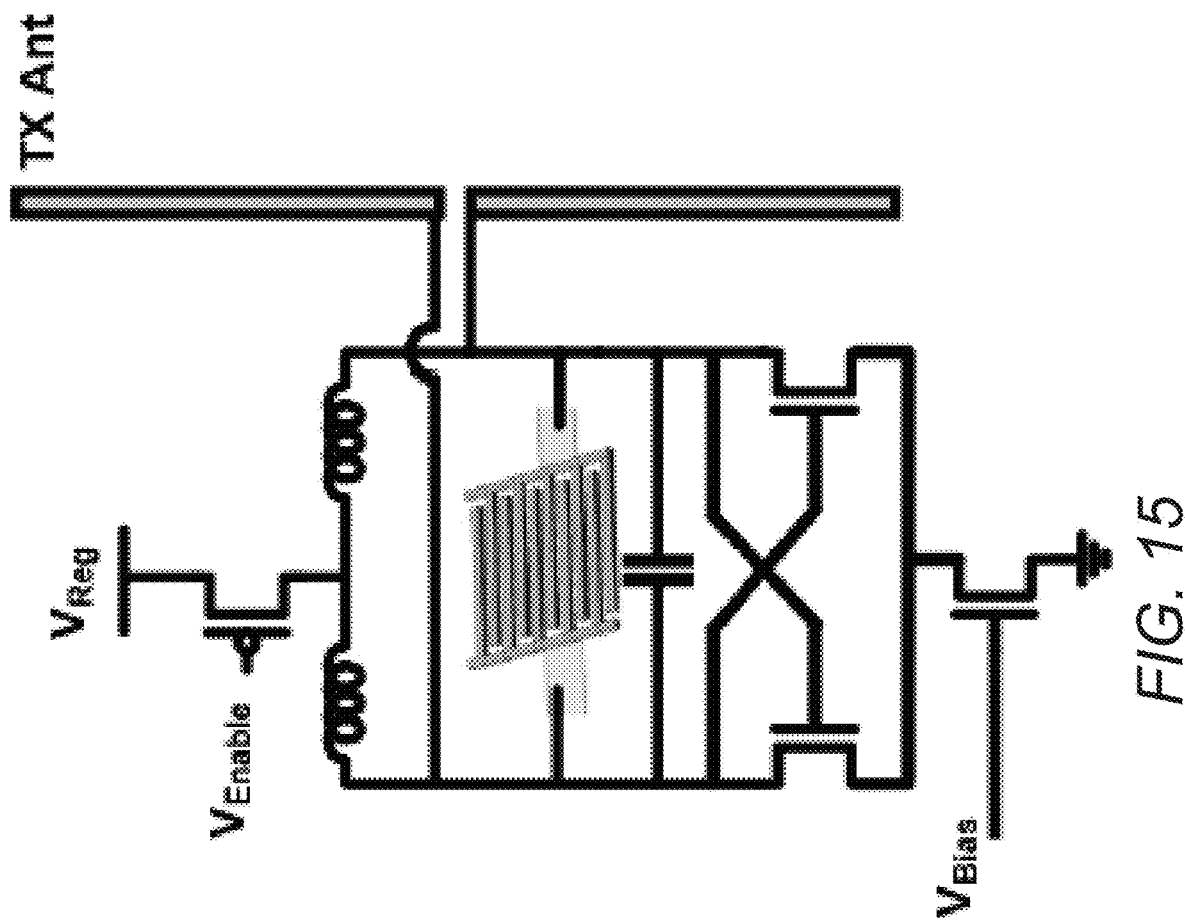
FIG. 15 illustrates a schematic of dielectric sensing VCO with TX on-chip antenna in accordance with several embodiments of the invention.

In certain embodiments, at this supply level, the oscillator may generate −25 dBm power to the TX on-chip antenna. In simulation, the free-running frequency can be 4 GHz. A schematic of an LC dielectric sensing sensor in accordance with several embodiments of the invention is illustrated in FIG. 15. Although FIG. 15 illustrates a particular schematic of an LC dielectric sensing sensor, any of a variety of architectures may be utilized as appropriate to the requirements of specific applications in accordance with embodiments of the invention. Additional details for designing dielectric sensing sensors, circuit design and techniques as related to, for example, FIG. 15, can be found in Pozar, David M. "Microwave engineering" John Wiley & Sons, 2009, Chapter 13, "Oscillators and Mixers", starting on page 604, and in Razavi, Behzad "RF microelectronics" Vol. 1, New Jersey: Prentice hall, 1998, Chapter 8 starting on page 497, and in Cheng, David Keun, "Field and wave electromagnetics", Pearson Education India, 1989, and in Razavi, Behzad, *"Design of analog CMOS Integrated Circuits"* 2001, the disclosures of which are hereby incorporated by reference in their entirety.

Measurement Result

Figure 16:
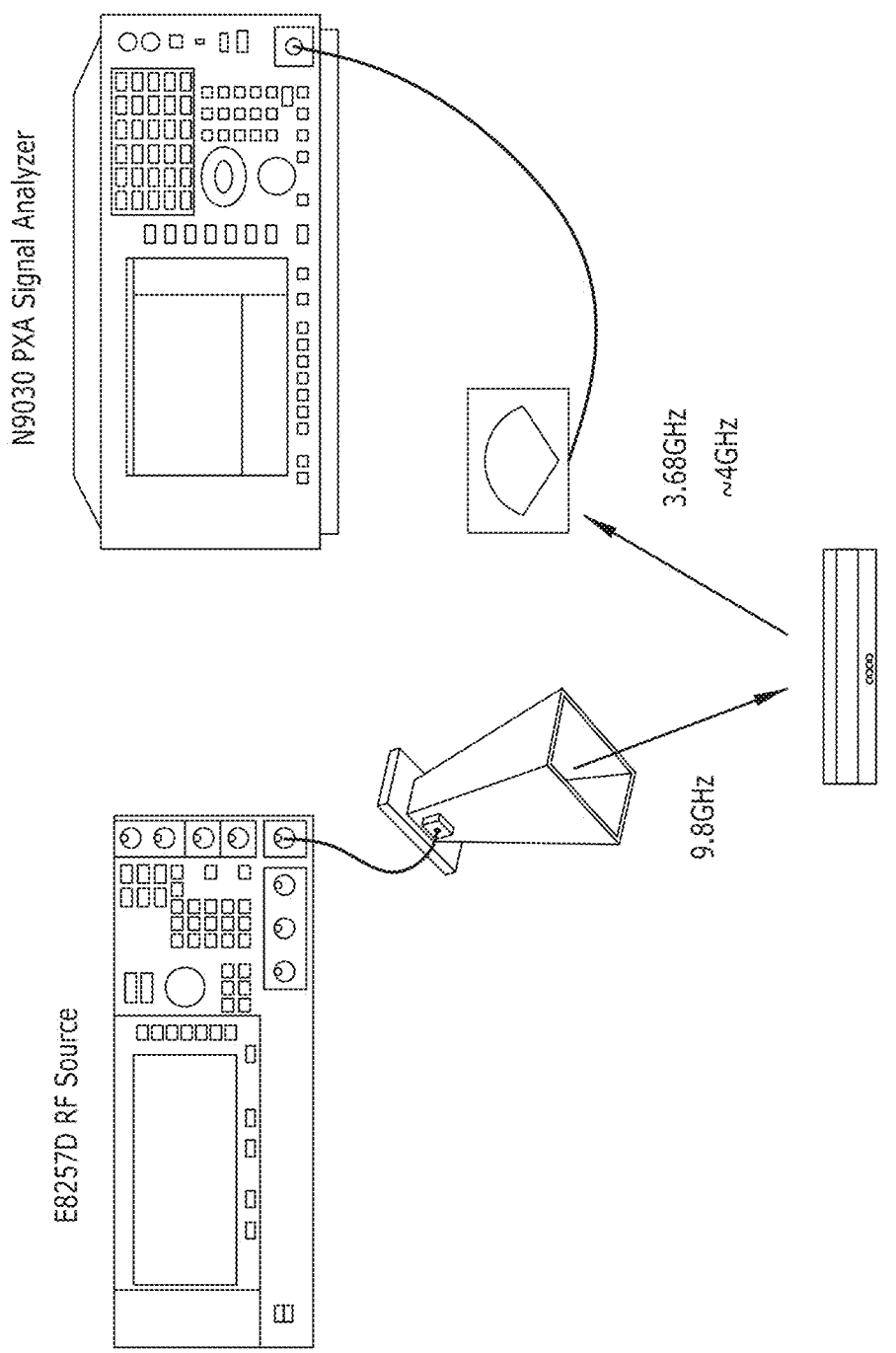
FIG. 16 illustrates measurement setup with oil on top of the chip in accordance with several embodiments of the invention.

Described below are certain measurement results for a dielectric sensing circuit in accordance with several embodiments of the invention. FIG. 16 illustrates a measurement setup in accordance with several embodiments of the invention. A Keysight E8257D RF source may generate an RF signal that is amplified by an X-band PA and then fed to a horn antenna. The horn antenna can be used to transmit electromagnetic waves with EIRP of 36 dBm at 9.8 GHz. The chip may be placed 6 cm away. The microchip may harvest the power and transmit the oscillator freerunning signal back to the RX slot-bowtie antenna in the frequency range of 3.6 GHz to 4 GHz. The receiving antenna can be connected to a Keysight PXA N9030A spectrum analyzer.

Figure 17:
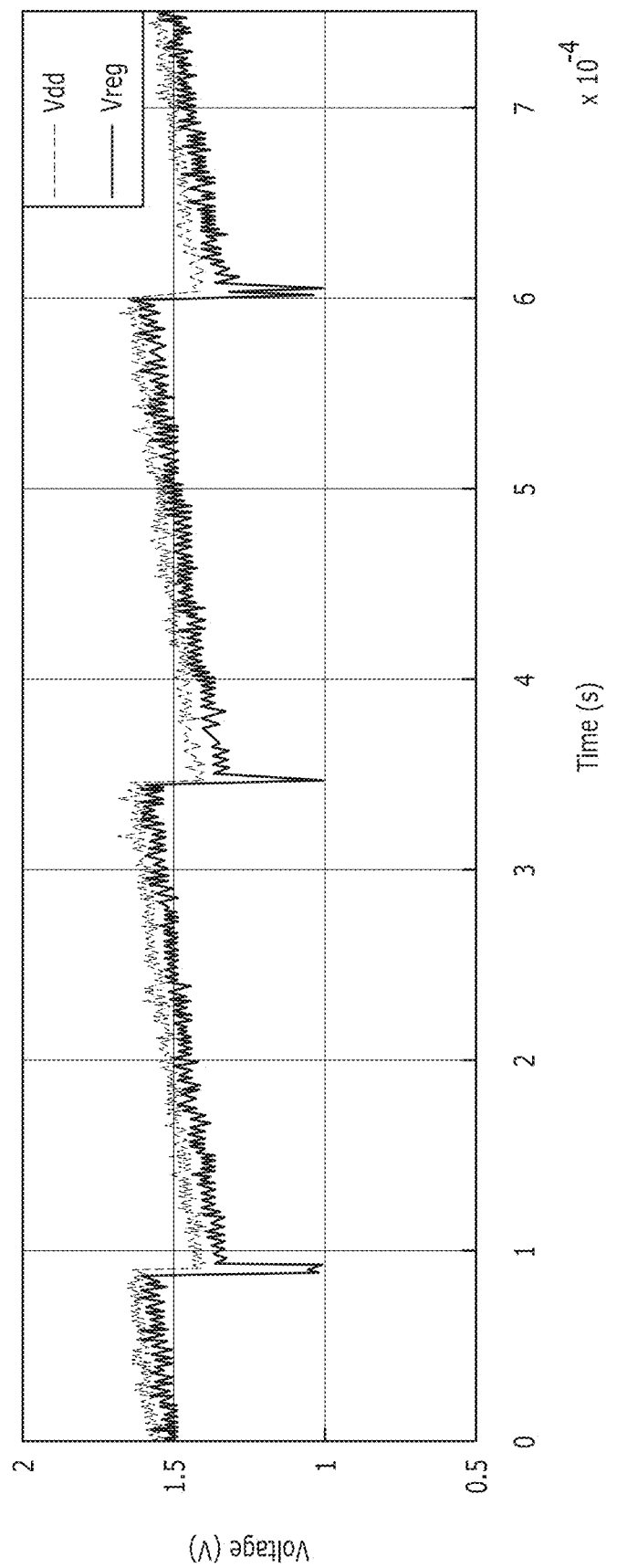
FIG. 17 illustrates measured transient signal of voltage on storage (Vdd) and regulated voltage after LDO (Vreg) in accordance with several embodiments of the invention.
Figure 18:
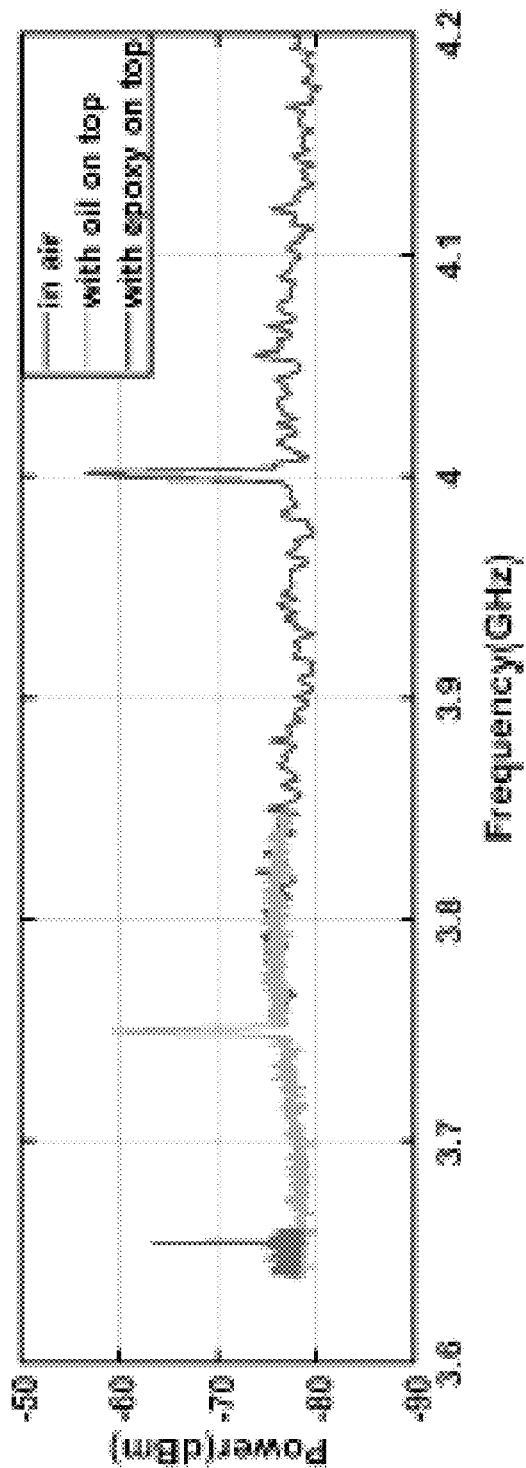
FIG. 18 illustrates transmitted signal spectrum from wirelessly-powered dielectric sensor, showing oscillation frequency of 4 GHz, 3.75 GHz, 3.66 GHz, with air, oil and epoxy on top of the chip respectively in accordance with several embodiments of the invention.
Figure 19:
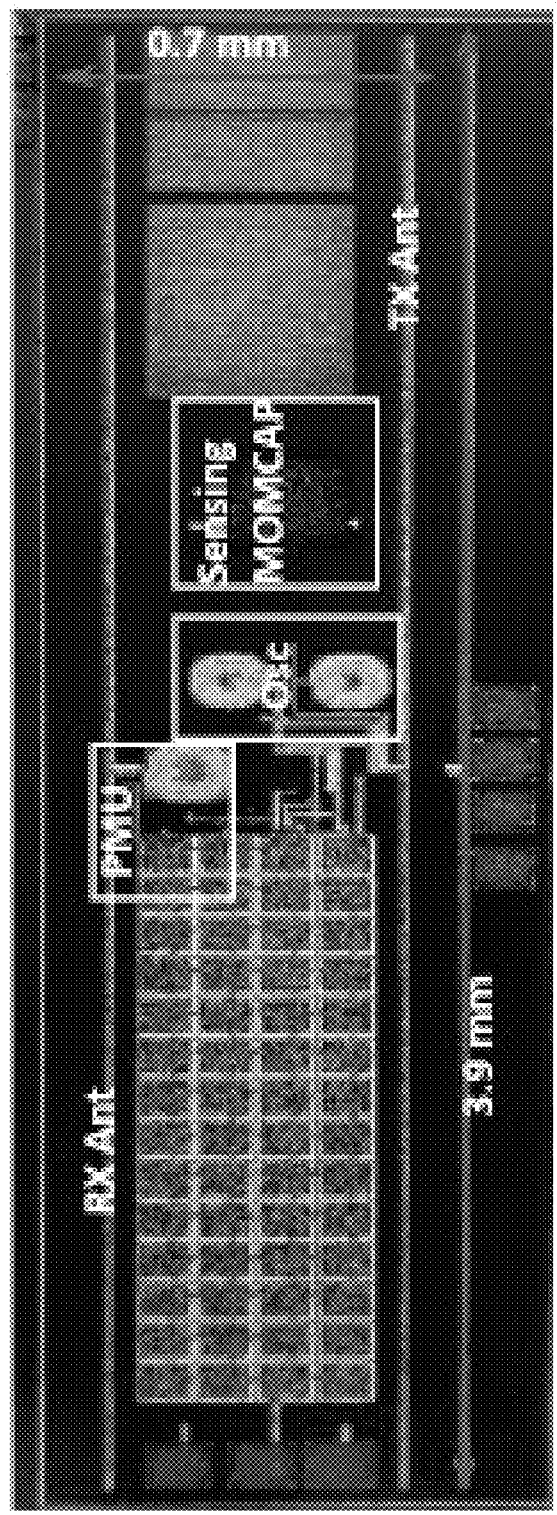
FIG. 19 illustrates a micrograph of the 3.9×0.7 mm$^2$ chip in accordance with several embodiments of the invention.

Transient signal of the voltage on storage capacitor and regulated voltage at LDO output in accordance with several embodiments of the invention are plotted in FIG. 17. As illustrated in FIG. 17, when the Vdd voltage is charged to 1.65 V, it may turn on the oscillator. Then the storage capacitor can be discharged to 1.3 V. The repetition rate can be tuned by adding an external storage capacitor or tuning the received RF power. The LDO regulated voltage may be 1 V, which can be used as the supply voltage for the oscillator. The received signal spectrum in accordance with several embodiments of the invention is illustrated in FIG. 18, demonstrating the oscillation frequency of the chip in different environments. The free-running frequency in air can be 4 GHz. The frequency may change to 3.75 GHz when oil is placed on top of the chip. It may change 3.66 GHz when an epoxy is used. This indicates the MOMCAP capacitance may increase to 236 fF and 265 fF when oil or epoxy is used. These values match well with the EM simulation results. A die micrograph of a dielectric sensor chip in accordance with several embodiments of the invention is illustrated in FIG. 19. The total chip size can be only 2.73 mm$^2$ that includes integrated on-chip dipole antennas. In many embodiments, the chip can be fabricated in a 180 nm CMOS SOI process and occupies an area of 3:9 0:7 mm$^2$, including the on-chip antennas and storage capacitor. The die photo of the chip in accordance with several embodiments is illustrated in FIG. 19. Although FIG. 19 illustrates a particular dielectric sensing chip fabricated in a 180 nm CMOS SOI process, any of a variety of chip sizes and fabrication processes may be utilized as appropriate to the requirements of specific applications in accordance with embodiments of the invention.

Accordingly, many embodiments provide a fully integrated wirelessly powered frequency-shift based dielectric sensor with on-chip antennas. In many embodiments, the sensor includes an energy-harvesting frontend, a power management unit, a dielectric sensing sensor, and on-chip receiving and transmitting antennas. In many embodiments, the chip has the ability to sense different dielectric material such as oil and epoxy by measuring the frequency shift of the oscillator. In many embodiments, the entire chip may be powered wirelessly through an on-chip antenna. In certain embodiments, the chip may have a maximum operating distance of 6 cm.

Although specific methods and systems for battery-less wirelessly powered dielectric sensors are discussed above, many different systems can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A wirelessly powered dielectric sensor, comprising:
    an RF-power receiving antenna that receives electromagnetic power;
    a power management unit (PMU) comprising a first capacitor to rectify and store the electromagnetic power; and
    a dielectric constant sensing sensor comprising an oscillator comprising a second capacitor and an inductor;
    wherein the PMU monitors harvested energy and operates the dielectric sensing sensor;
    wherein the dielectric sensing sensor senses a dielectric constant of a material that is in close proximity by capacitance change of the second capacitor, and which sensed capacitance change of the second capacitor produces a shift in the oscillation frequency of the oscillator.

2. The wirelessly powered dielectric sensor of claim 1, wherein the PMU further comprises a voltage reference circuit, a comparator, a low drop-out (LDO) regulator, wherein the first capacitor is an on-chip storage capacitor.

3. The wirelessly powered dielectric sensor of claim 2, wherein the PMU monitors a voltage on the first capacitor and turns a transmitter circuit on when there is sufficient energy in the first capacitor.

4. The wirelessly powered dielectric sensor of claim 3, wherein the PMU generates enable signals to turn on the low drop-out regulator to generate a regulated voltage $V_{reg}$ for the dielectric sensing sensor and to turn on the dielectric sensing sensor.

5. The wirelessly powered dielectric sensor of claim 1, wherein the receiving antenna is an on-chip antenna.

6. The wirelessly powered dielectric sensor of claim 1, wherein the first capacitor is an on-chip capacitor.

7. The wirelessly powered dielectric sensor of claim 1, further comprising a transmitting on-chip antenna, wherein the transmitting on-chip antenna is used to wirelessly transmit a signal.

8. The wirelessly powered dielectric sensor of claim 7, wherein the oscillator is a dielectric sensing oscillator which drives the transmitting on-chip antenna to radiate back a signal at the oscillation frequency of the oscillator.

9. The wirelessly powered dielectric sensor of claim 7, wherein the transmitting on-chip antenna is used to transmit the signal using at least one of a wired communication channel or a wireless communication channel.

10. The wirelessly powered dielectric sensor of claim 1, wherein the oscillator produces a frequency shift depending on the value of the dielectric constant being measured.

11. The wirelessly powered dielectric sensor of claim 1, wherein the PMU operates the dielectric sensing sensor in duty cycle mode.

12. The wirelessly powered dielectric sensor of claim 1, wherein the dielectric sensing sensor is used to receive a command where there is a nonconductive isolating layer between a user providing the command and the wirelessly powered dielectric sensor.

13. The wirelessly powered dielectric sensor of claim 1, wherein the second capacitor of the dielectric sensing sensor comprises a metaloxide-metal capacitor (MOMCAP) that provides different capacitance for different materials.

14. A method for wirelessly powering a dielectric sensor, comprising
    receiving electromagnetic power using an RF-power receiving antenna;
    rectifying and storing the electromagnetic power using a first capacitor included in a power management unit (PMU);
    sensing a dielectric constant using a dielectric constant sensing sensor comprising an oscillator comprising a second capacitor and an inductor;

wherein the PMU monitors harvested energy and operates the dielectric sensing sensor;

wherein the dielectric sensing sensor senses a dielectric constant of a material that is in close proximity by capacitance change of the second capacitor, and which sensed capacitance change of the second capacitor produces a shift in the oscillation frequency of the oscillator.

15. The method of claim 14, wherein the PMU further comprises a voltage reference circuit, a comparator, a low drop-out (LDO) regulator, wherein the first capacitor is an on-chip storage capacitor.

16. The method of claim 15, wherein the PMU monitors a voltage on the first capacitor and turns a transmitter circuit on when there is sufficient energy in the first capacitor.

17. The method of claim 16, wherein the PMU generates enable signals to turn on the low drop-out regulator to generate a regulated voltage Vreg for the dielectric sensing sensor and to turn on the dielectric sensing sensor.

18. The method of claim 14, wherein the receiving antenna is an on-chip antenna.

19. The method of claim 14, wherein the first capacitor is an on-chip capacitor.

20. The method of claim 14, further comprising wirelessly transmitting a signal using a transmitting on-chip antenna.

* * * * *